US012383658B2

(12) United States Patent
Biggins et al.

(10) Patent No.: US 12,383,658 B2
(45) Date of Patent: *Aug. 12, 2025

(54) HIGH STRENGTH BIOMEDICAL MATERIALS

(71) Applicant: Access Vascular, Inc., Billerica, MA (US)

(72) Inventors: James F. Biggins, Waltham, MA (US); Michael Bassett, Hampton, NH (US); Daniel T. Donahue, Cambridge, MA (US)

(73) Assignee: Access Vascular, Inc., Billerica, MA (US)

( * ) Notice: Subject to any disclaimer, the term of this patent is extended or adjusted under 35 U.S.C. 154(b) by 182 days.

This patent is subject to a terminal disclaimer.

(21) Appl. No.: 17/841,813

(22) Filed: Jun. 16, 2022

(65) Prior Publication Data

US 2022/0378984 A1    Dec. 1, 2022

Related U.S. Application Data

(63) Continuation of application No. 16/586,757, filed on Sep. 27, 2019, now Pat. No. 11,389,570, which is a continuation of application No. 15/388,820, filed on Dec. 22, 2016, now Pat. No. 10,471,183.

(60) Provisional application No. 62/271,150, filed on Dec. 22, 2015.

(51) Int. Cl.
| | | |
|---|---|---|
| *A61L 29/04* | (2006.01) |
| *A61L 17/10* | (2006.01) |
| *A61L 27/16* | (2006.01) |
| *A61L 27/56* | (2006.01) |
| *A61L 29/02* | (2006.01) |
| *A61L 29/14* | (2006.01) |
| *A61L 29/16* | (2006.01) |
| *A61L 29/18* | (2006.01) |
| *A61L 33/00* | (2006.01) |
| *A61L 33/06* | (2006.01) |
| *B29C 48/00* | (2019.01) |
| *B29C 48/78* | (2019.01) |
| *B29C 48/86* | (2019.01) |
| *B29K 105/04* | (2006.01) |
| *B29L 31/00* | (2006.01) |
| *C08J 9/00* | (2006.01) |
| *C08J 9/28* | (2006.01) |
| *D01F 1/08* | (2006.01) |
| *D01F 6/14* | (2006.01) |
| *D01F 6/50* | (2006.01) |
| *A61M 25/00* | (2006.01) |
| *B29C 48/05* | (2019.01) |
| *B29C 67/00* | (2017.01) |

(52) U.S. Cl.
CPC ............ *A61L 29/041* (2013.01); *A61L 17/10* (2013.01); *A61L 27/16* (2013.01); *A61L 27/56* (2013.01); *A61L 29/02* (2013.01); *A61L 29/049* (2013.01); *A61L 29/146* (2013.01); *A61L 29/16* (2013.01); *A61L 29/18* (2013.01); *A61L 33/007* (2013.01); *A61L 33/064* (2013.01); *B29C 48/00* (2019.02); *B29C 48/78* (2019.02); *C08J 9/0061* (2013.01); *C08J 9/0066* (2013.01); *C08J 9/28* (2013.01); *D01F 1/08* (2013.01); *A61L 2300/42* (2013.01); *A61L 2400/12* (2013.01); *A61M 25/005* (2013.01); *B29C 48/05* (2019.02); *B29C 48/865* (2019.02); *B29C 67/0029* (2013.01); *B29K 2105/04* (2013.01); *B29L 2031/753* (2013.01); *C08J 2201/03* (2013.01); *C08J 2201/0546* (2013.01); *C08J 2205/042* (2013.01); *C08J 2205/044* (2013.01); *C08J 2207/10* (2013.01); *C08J 2329/04* (2013.01); *C08J 2433/02* (2013.01); *D01F 6/14* (2013.01); *D01F 6/50* (2013.01)

(58) Field of Classification Search
None
See application file for complete search history.

(56) References Cited

U.S. PATENT DOCUMENTS

| 3,220,960 A | 11/1965 | Vaclavkova |
| 3,566,874 A | 3/1971 | Shepherd et al. |
| 3,995,623 A | 12/1976 | Blake et al. |
| 4,024,873 A | 5/1977 | Antoshkiw et al. |
| 4,026,296 A | 5/1977 | Stoy et al. |

(Continued)

FOREIGN PATENT DOCUMENTS

| CN | 1579601 A | 2/2005 |
| CN | 102580145 A | 7/2012 |

(Continued)

OTHER PUBLICATIONS

Peppas, N. A., and D. Tennenhouse. "Semicrystalline poly (vinyl alcohol) films and their blends with poly (acrylic acid) and poly (ethylene glycol) for drug delivery applications." Journal of Drug Delivery Science and Technology 14.4 (2004): 291-297. (Year: 2004).*

(Continued)

*Primary Examiner* — Bethany P Barham
*Assistant Examiner* — Peter Anthopolos
(74) *Attorney, Agent, or Firm* — Wolf, Greenfield & Sacks, P.C.

(57) ABSTRACT

High strength biomedical materials and processes for making the same are disclosed. Included in the disclosure are nanoporous hydrophilic solids that can be extruded with a high aspect ratio to make high strength medical catheters and other devices with lubricious and biocompatible surfaces.

21 Claims, 17 Drawing Sheets

(56) References Cited

U.S. PATENT DOCUMENTS

| | | | |
|---|---|---|---|
| 4,073,733 A | 2/1978 | Yamauchi et al. | |
| 4,379,874 A | 4/1983 | Stoy | |
| 4,543,102 A | 9/1985 | Defago et al. | |
| 4,663,358 A | 5/1987 | Hyon et al. | |
| 4,943,618 A | 7/1990 | Stoy et al. | |
| 5,061,254 A | 10/1991 | Karakelle et al. | |
| 5,225,120 A * | 7/1993 | Graiver | B01D 69/08 264/28 |
| 5,336,205 A | 8/1994 | Zenzen et al. | |
| 5,443,727 A | 8/1995 | Gagnon | |
| 5,449,382 A | 9/1995 | Dayton | |
| 5,508,036 A | 4/1996 | Bakker et al. | |
| 5,523,335 A | 6/1996 | Whyzmuzis et al. | |
| 5,578,075 A | 11/1996 | Dayton | |
| 5,601,538 A | 2/1997 | Deem | |
| 5,679,400 A | 10/1997 | Tuch | |
| 5,688,459 A | 11/1997 | Mao et al. | |
| 5,820,918 A | 10/1998 | Ronan et al. | |
| 5,928,279 A | 7/1999 | Shannon et al. | |
| 6,099,562 A | 8/2000 | Ding et al. | |
| 6,231,605 B1 | 5/2001 | Ku | |
| 6,271,278 B1 | 8/2001 | Park et al. | |
| 6,656,206 B2 | 12/2003 | Corcoran et al. | |
| 6,706,024 B2 | 3/2004 | Modak et al. | |
| 7,112,298 B2 | 9/2006 | Kampa et al. | |
| 7,329,695 B2 | 2/2008 | Tucker et al. | |
| 7,455,674 B2 | 11/2008 | Rose | |
| 7,485,670 B2 | 2/2009 | Ruberti et al. | |
| 7,619,009 B2 | 11/2009 | Ruberti et al. | |
| 7,631,760 B2 | 12/2009 | Guelzow et al. | |
| 7,745,532 B2 | 6/2010 | Ruberti et al. | |
| 7,845,670 B2 | 12/2010 | Oberg | |
| 8,017,139 B2 | 9/2011 | Thomas et al. | |
| 8,313,760 B2 | 11/2012 | Hunter et al. | |
| 8,470,035 B2 * | 6/2013 | Cruise | A61L 31/146 523/115 |
| 8,541,484 B2 | 9/2013 | Choi et al. | |
| 8,637,063 B2 | 1/2014 | Kopesky et al. | |
| 8,784,893 B2 | 7/2014 | Daniloff et al. | |
| 8,821,583 B2 | 9/2014 | Myung et al. | |
| 9,216,268 B2 | 12/2015 | Liu et al. | |
| 10,182,985 B2 | 1/2019 | Bellinger et al. | |
| 10,471,183 B2 | 11/2019 | Biggins et al. | |
| 10,485,898 B2 | 11/2019 | Biggins et al. | |
| 11,389,570 B2 | 7/2022 | Biggins et al. | |
| 11,577,008 B2 | 2/2023 | Bassett et al. | |
| 11,992,627 B2 | 5/2024 | Bassett et al. | |
| 2001/0002411 A1 | 5/2001 | Ronan et al. | |
| 2002/0055710 A1 | 5/2002 | Tuch | |
| 2002/0138154 A1 | 9/2002 | Li et al. | |
| 2004/0092653 A1 | 5/2004 | Ruberti et al. | |
| 2004/0247867 A1 | 12/2004 | Chaouk et al. | |
| 2006/0205862 A1 | 9/2006 | Muller et al. | |
| 2006/0240059 A1 | 10/2006 | Bavaro et al. | |
| 2006/0287650 A1 | 12/2006 | Cao et al. | |
| 2007/0129690 A1 | 6/2007 | Rosenblatt et al. | |
| 2008/0065010 A1 | 3/2008 | Bavaro et al. | |
| 2008/0075628 A1 | 3/2008 | Judd et al. | |
| 2008/0160062 A1 | 7/2008 | Richard et al. | |
| 2008/0208347 A1 | 8/2008 | Muratoglu et al. | |
| 2009/0010983 A1 | 1/2009 | Melvik et al. | |
| 2009/0075267 A1 | 3/2009 | Siena et al. | |
| 2009/0076495 A2 | 3/2009 | Dando et al. | |
| 2010/0087788 A1 | 4/2010 | Rosenblatt et al. | |
| 2010/0105801 A1 | 4/2010 | Choi | |
| 2010/0106103 A1 | 4/2010 | Ziebol et al. | |
| 2010/0145286 A1 | 6/2010 | Zhang et al. | |
| 2010/0152708 A1 | 6/2010 | Li et al. | |
| 2010/0204800 A1 | 8/2010 | Thomas et al. | |
| 2010/0210752 A1 | 8/2010 | Muratoglu et al. | |
| 2010/0234815 A1 | 9/2010 | Do et al. | |
| 2011/0000846 A1 | 1/2011 | Ishizuka et al. | |
| 2011/0027181 A1 | 2/2011 | Amodei et al. | |
| 2011/0091515 A1 | 4/2011 | Zilberman et al. | |
| 2011/0190683 A1 | 8/2011 | Gellman et al. | |
| 2011/0244010 A1 | 10/2011 | Doshi | |
| 2013/0046346 A1 | 2/2013 | Thorwarth et al. | |
| 2013/0338431 A1 | 12/2013 | Shalon et al. | |
| 2014/0045398 A1 | 2/2014 | Zhang et al. | |
| 2014/0058251 A1 | 2/2014 | Stigall et al. | |
| 2014/0178446 A1 | 6/2014 | Zhu et al. | |
| 2014/0287179 A1 | 9/2014 | Kamioka et al. | |
| 2016/0015863 A1 | 1/2016 | Gupta et al. | |
| 2016/0136389 A1 | 5/2016 | Christian et al. | |
| 2016/0175483 A1 | 6/2016 | Zeitels et al. | |
| 2017/0143952 A1 | 5/2017 | Siess et al. | |
| 2017/0173219 A1 | 6/2017 | Biggins et al. | |
| 2017/0182223 A1 | 6/2017 | Biggins et al. | |
| 2017/0340867 A1 | 11/2017 | Acisano, III | |
| 2018/0200185 A1 | 7/2018 | Labib et al. | |
| 2018/0250116 A1 | 9/2018 | Mourhatch et al. | |
| 2018/0369454 A1 | 12/2018 | Mannarino et al. | |
| 2019/0167942 A1 | 6/2019 | Schonfeldt | |
| 2020/0093965 A1 | 3/2020 | Biggins et al. | |
| 2020/0205959 A1 | 7/2020 | Mourhatch et al. | |
| 2020/0230295 A1 | 7/2020 | Mannarino et al. | |
| 2021/0069468 A1 | 3/2021 | Keating et al. | |
| 2021/0275774 A1 | 9/2021 | Doherty et al. | |
| 2022/0088348 A1 | 3/2022 | Bassett et al. | |
| 2023/0256141 A1 | 8/2023 | Bassett et al. | |
| 2024/0399110 A1 | 12/2024 | Bassett et al. | |

FOREIGN PATENT DOCUMENTS

| | | |
|---|---|---|
| CN | 102634865 A | 8/2012 |
| EP | 0 532 037 A1 | 3/1993 |
| EP | 2075014 B1 | 7/2011 |
| GB | 2203158 A | 10/1988 |
| JP | S52-21420 A | 2/1977 |
| JP | S55-106162 A | 8/1980 |
| JP | S58-014906 A | 1/1983 |
| JP | S61-226061 A | 10/1986 |
| JP | S62-11460 A | 1/1987 |
| JP | H01-299564 A | 12/1989 |
| JP | H10-306191 A | 11/1998 |
| JP | H11-130929 A | 5/1999 |
| JP | 2002-360685 A | 12/2002 |
| JP | 2007-500764 A | 1/2007 |
| JP | 2012-251057 A | 12/2012 |
| JP | 5820918 B1 | 11/2015 |
| JP | 2016-210992 A | 12/2016 |
| JP | 2014-065681 A | 4/2017 |
| JP | 2017-141477 A | 8/2017 |
| KR | 2018-0110695 A | 10/2018 |
| WO | WO 92/07899 A2 | 5/1992 |
| WO | WO 97/41180 A1 | 11/1997 |
| WO | WO 99/44665 A2 | 9/1999 |
| WO | WO 01/68746 A1 | 9/2001 |
| WO | WO 2007/002004 A2 | 1/2007 |
| WO | WO 2012/122023 A2 | 9/2012 |
| WO | WO 2014/063711 A1 | 5/2014 |
| WO | WO 2014/077886 A1 | 5/2014 |
| WO | WO 2017/112878 A1 | 6/2017 |
| WO | WO 2018/237166 A1 | 12/2018 |
| WO | WO 2021/168284 A1 | 8/2021 |

OTHER PUBLICATIONS

International Search Report and Written Opinion for PCT/US2016/068357 mailed Apr. 5, 2017.

[No Author Listed], Dimethyl Sulfoxide Physical Properties. Gaylord Chemical Company, L.L.C., Bulletin 101. Jun. 2014. 14 pages.

Chirilia et al., Poly(2-hydroxyethyl methacrylate) sponges as implant materials: in vivo and in vitro evaluation of cellular invasion. Biomaterials. 1993;14(1):26-38.

Fukumori et al., Significant improvement of mechanical properties for polyvinyl alcohol film prepared from freeze/thaw cycled gel. Open Journal of Organic Polymer Materials. 2013;3:110-116.

Kang, The synthesis of nanoporous hydrogels using sacrificial block copolymers. Dissertation. Massachusetts Institute of Technology. Jul. 21, 2006. 106 pages.

(56) References Cited

OTHER PUBLICATIONS

Peppas et al., Semicrystalline poly(vinyl alcohol) films and their blends with poly(acrylic acid) and poly(ethylene glycol) for drug delivery applications. Journal of Drug Delivery Science and Technology. 2004;14(4):291-297.

Sandeman et al., Adsorption of anionic and cationic dyes by activated carbons, PVA hydrogels, and PVA/AC composite. J Colloid Interface Sci. Jun. 15, 2011;358(2):582-92. doi: 10.1016/j.jcis.2011.02.031. Epub Feb. 17, 2011.

Speybrouck et al., Successful superior thyroid artery embolisation using microporous beads. European Society for Vascular Surgery. 2012;24:e5-e6.

Hamada et al., Melting point of polyvinyl alcohol. Polym Chem. 1966;23(254):395-9.

\* cited by examiner

HIGH STRENGTH BIOMEDICAL MATERIALS

RELATED APPLICATIONS

This Application is a Continuation of U.S. application Ser. No. 16/586,757, filed Sep. 27, 2019, entitled "HIGH STRENGTH BIOMEDICAL MATERIALS", which is a Continuation of U.S. application Ser. No. 15/388,820, filed Dec. 22, 2016, entitled "HIGH STRENGTH BIOMEDICAL MATERIALS", which is a Non-Prov of Prov (35 USC 119 (e)) of U.S. Application Ser. No. 62/271,150, filed Dec. 22, 2015, entitled "NANOPOROUS BIOMATERIALS". The entire contents of these applications are incorporated herein by reference in their entirety.

TECHNICAL FIELD

The technical field relates to porous biomaterials, including high strength hydrophilic nanoporous biomaterials for medical devices.

SUMMARY OF INVENTION

Biomaterials useful to make medical devices are disclosed herein. Materials and methods are provided herein for the fabrication of tough, lubricious biocompatible biomaterials for a variety of medical device applications. New processing techniques have been used to make the biomaterials with superior properties such as strength and hemocompatibility. Included herein are methods for extrusion of hydrophilic polymers to create high strength, hemocompatible, nanoporous biomaterials or other materials. These processes can be performed without the use of chemical crosslinkers or radiation crosslinking.

An embodiment is a process for making a hydrophilic material comprising heating a mixture that comprises at least one water soluble polymer and a solvent to a temperature above a melting point of the polymer, forming the mixture, and passing the mixture into a solvent-removing environment. Extrusion may be used to form the mixture, with the mixture being formed into a continuous porous solid as it passes through a die. A nanoporous solid may be made that has a Young's modulus of at least 5 MPa at equilibrium water content (EWC) of the porous solid. Extrusion may be used to form high strength materials with a high aspect ratio, including tubulars useful as catheters.

An embodiment is a polymeric material comprising a hydrophilic porous solid, with the porous solid having a solids content of at least 33% w/w and a Young's modulus of at least 5 MPa, at equilibrium water content (EWC). The material may be formed with a high aspect ratio, for example, more than 10:1, including materials formed as catheters.

DETAILED DESCRIPTION OF INVENTION

Figure 1:
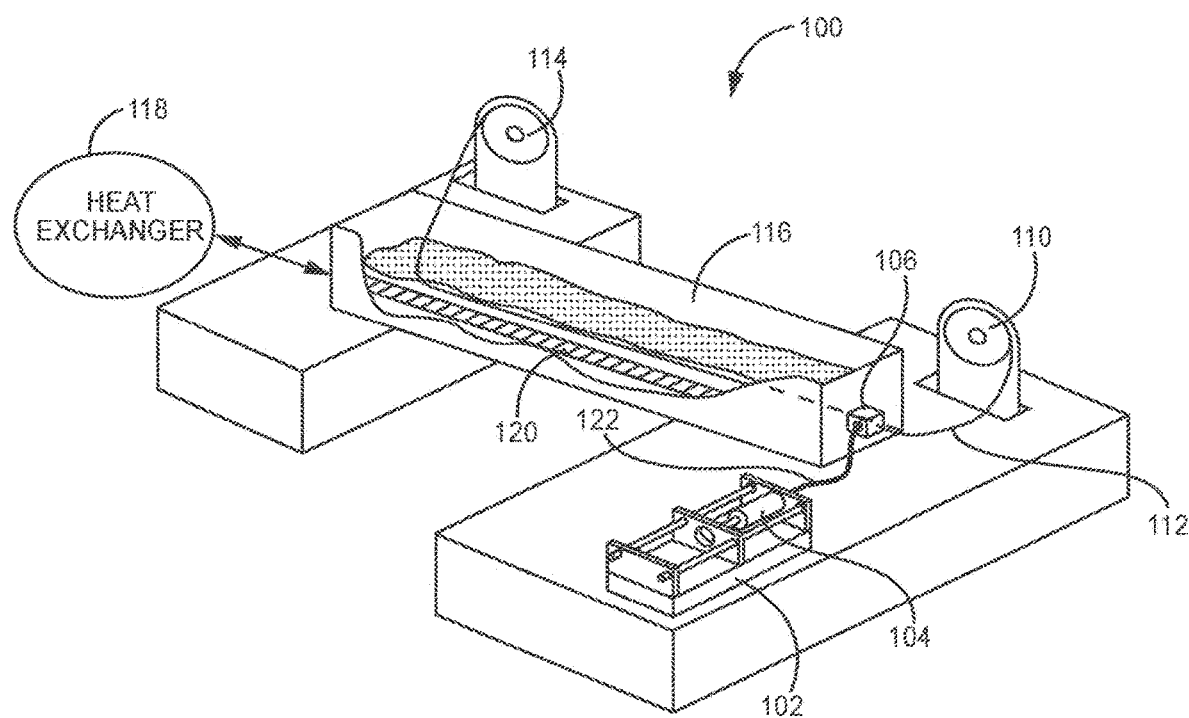
FIG. 1 is a schematic of an extrusion apparatus to form a continuous form with a cut-away view of a side of the bath.
Figure 2:
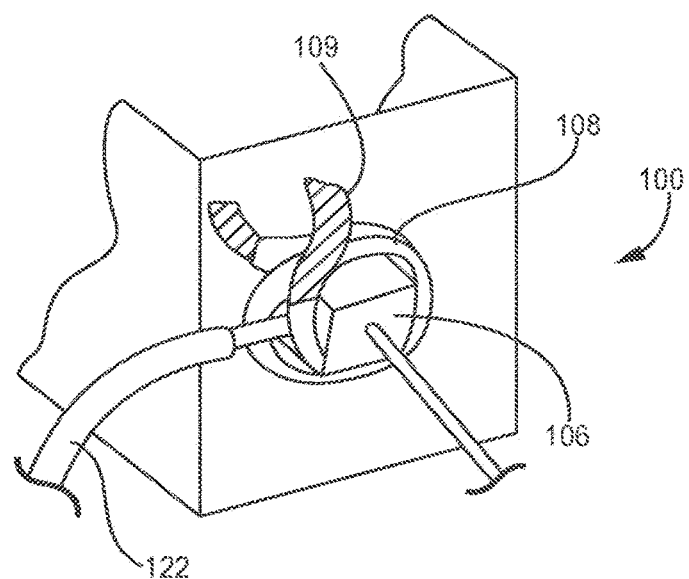
FIG. 2 is an enlarged view of a portion of the apparatus of FIG. 1 depicting the die head in perspective as viewed from the outside of the bath.
Figure 3:
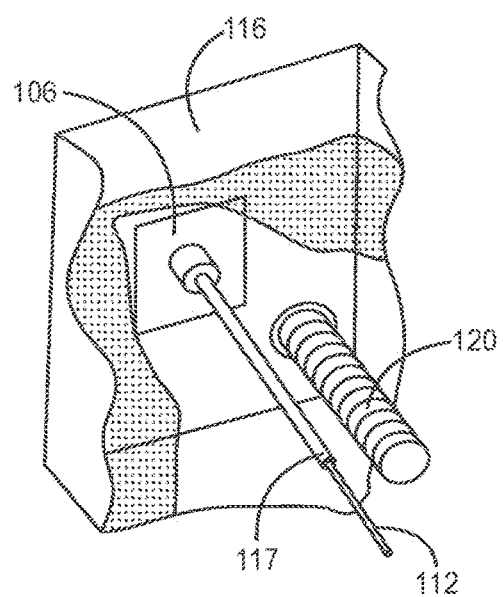
FIG. 3 is an enlarged view of a portion of the apparatus of FIG. 1 depicting the die head as disposed in the bath.
Figure 4:
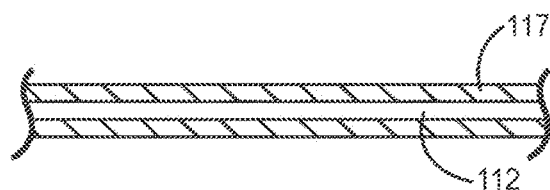
FIG. 4 is a longitudinal cross section of a portion of a continuous porous solid as formed with the apparatus of FIG. 1.

Materials, methods, and uses are set forth herein for a biomaterial comprising a medically acceptable porous solid. These materials can be made as tough, high strength materials having lubricious and biocompatible surfaces. Nanoporous and microporous solids are described herein that have a particularly high Young's modulus and tensile strength. A nanoporous material is a solid that contains interconnected pores of up to 100 nm in diameter. Processes for making hydrogels are also described. Hydrophilic polymers may be used to make these various porous solids so that a hydrophilic solid is obtained. The water content of a nanoporous or a microporous solid can be high, e.g., 50% w/w at EWC. The water content of a hydrogel may be higher, for example, up to 90% w/w in principle. The porous solid materials can be used to make various devices, including medical catheters and implants with significant reductions in adsorption and/or adhesion of biological components to their surfaces.

Processes for making the material can include extrusion so that devices with a high aspect ratio may be created. An embodiment of a process for making the materials involves heating a mixture that comprises at least one water soluble polymer and a solvent to a temperature above the melting point of the polymer solution forming the mixture in a solvent-removing environment resulting in a crosslinked matrix, and continuing to remove the solvent until the crosslinked matrix is a microporous or a nanoporous solid material. The crosslinking can take place while cooling the mixture and/or in the solvent-removing environment.

Extrusion of Polymeric Materials

Various techniques for making solid plastic materials are known. These conventionally include processes that force a polymeric material through an opening under conditions where the polymeric material forms into a solid plastic as it passes through the opening. Typically there is a heating phase to soften or melt the polymer, a shaping/forming phase wherein the polymer is in a flowable form and under some kind of constraint, and a cooling phase wherein the shaped/formed polymer is cooled to a temperature at which it retains its shape. The plastic may undergo some changes after it passes through the opening, such as shrinkage, solvent removal, or crosslinking but its shape is fixed when it solidifies. Thermoplastics can be remelted. Some thermosets form strong interchain and/or intra-chain bonds that are non-covalent crosslinks, and are referred to as physical crosslinks to distinguish them from covalent bonds. Thermosets are formed irreversibly with covalent crosslinks. Examples of forming processes are thermoforming, molding processes, and extrusion processes. Extrusion processes typically involve forcing a polymeric material through a shaped die under pressure. Pellets of polymer are commonly fed into a hopper that enters a screw extruder that compresses and melts the polymer as it is conveyed to the die. After passing through an opening in the dye, the polymer rapidly cools and sets in a solid shape. Extrusion can also include a drawing process. Many complex shapes can be thrilled with extrusion processes, including tubes with one or more lumens, coatings, layered coatings, filaments, hollow profiled objects, objects with cross sections that are round, square polygonal, or complex, and copolymeric extrusions involving multiple polymers combined in the extruder or die. The term die is used broadly herein to encompass openings that polymers pass through in an extrusion process to form a solid, and includes dies that involve one or more of a mandrel, combinations of dies, port hole dies, dies with a plurality of openings that cooperate to make an extruded product, dies that cooperate with a core, dies that cooperate with core tubing, core wire, blown air or gas that serves as a core, or slit dies. A core is useful to provide a lumen for a continuously extruded product and may be used temporarily for a device with a hollow lumen or permanently in the case of a coated device, for example a coated wire. Almost any shape can be created with a die so long as the created shape has a continuous profile. The term continuous is a term of art that refers to theoretically producing indefinitely long material even through a semi-continuous, intermittent, or other processes cart be used.

Extrusion processes conventionally involve heating a polymer and passing it out of a die while it is hot to be rapidly cooled so as to set the plastic shape. The choice of temperatures and conditions depends on factors such as the polymer's chemical composition and molecular weight, melting temperature (Tm), glass transition temperature (Tg), presence of crosslinks, and effects caused by solvents if they are present. Tm marks a transition between a crystalline or semi-crystalline phase to a liquid amorphous phase. Tg marks a temperature at which amorphous polymers undergo a transition from a rubbery, viscous liquid, to a brittle, glassy amorphous solid on cooling. Amorphous polymers have a Tg but do not have a specific melting point, Tm. A conventional extrusion process generally involves a processing the polymer at a high temperature while it is in the extruder, with temperatures of more than 150.degree. C. being typical.

Herein is disclosed a new process that provides for extrusion of high strength materials. Certain embodiments of the process provide one or more of: removal of a solvent from a hydrophilic polymer-solvent mixture as the material is extruded, extruding at a cold temperature, extruding into a solvent-removing environment, and further removal of solvent for a period of time after extrusion. Further, an annealing phase may also be included.

FIGS. 1-4 depict an embodiment of an apparatus to make the materials. The device 100 as depicted has syringe pump 102 to accept at least one syringe 104, an optional heating jacket (not shown) to heat the syringes, die head 106, heating element 108 and power cables 109 for the same, providing heating as needed for die head 106 (detail not shown in FIG. 1), dispensing spool 110 for core tubing 112, uptake spool 114 and motor (not shown) for core tubing, bath 116 for the extruded material 117, with the bath having temperature control for cooling or heating, depicted as heat exchanger 118 that comprises heat exchanging pipe 120 in bath 116. Die head 106 accepts the core tubing 110 which passes there through. Feed line 122 from the syringes to die head 106 provides a feed to device 100. A system for this embodiment may further include a weigh station, a jacketed vessel for heating and mixing solutions for loading into the syringes, and a solvent-removal environment for further drying of tubing removed from bath 116. The system may also have a heating station for annealing the tubing or other extrusion product with heat when desired. Core tubing made of PTFE is useful, and wires, air, non-solvent liquid or other materials may be used for a core.

In use, by way of example, a polymer is heated in a suitable solvent in a jacketed vessel and placed into syringe 104. One or more polymers may be present and a radiopaque agent or other additive may be added. One or more syringes may be used with the same or different mixtures. The syringe(s) of the polymer are heated to a predetermined temperature of no more than 80-95.degree. C. and degassed before extrusion. Syringe 104 is mounted on syringe pump 102 with a wrap heater to maintain temperature during extrusion. Core 112 is looped through die head 106, e.g., a heated out-dwelling die head, which feeds into extrusion bath 116, and then attached to puller wheel 114 that is driven by a motor. Temperature of the bath is controlled using heat exchanger 118, such as a chiller; extruded materials are typically extruded at temperatures ranging from −30.degree. C. to 75.degree. C.; other temperatures may be used, and 0.degree. C. is a generally useful temperature setting for extrusion. Artisans will immediately appreciate that all ranges and values between the explicitly stated bounds are contemplated, with, e.g., any of the following being available as an upper or lower limit: −30, −25, −20, −15, −10, −5, 0, 5, 10, 15, 20, 25, 30, 35, 40, 45, 50, 55, 60, 65, 70, 75.degree. C. Puller wheel 114 motor speed can be controlled to adjust outer diameter gauge size around core 112. Adjusting die size, material feed rate, tubing core diameter, and puller speed play roles in adjusting final tubing gauge, e.g., in embodiments wherein a catheter is made. Polymer feed rates are adjustable, e.g., by control of syringe pump 102 in this embodiment. Connectors 122 join the one or more syringes to die head 106. Many pumps and other tools for controllably feeding a polymer solution are known. The apparatus and method can be adapted for a drawing process although alternative feed processes are available. Artisans reading this disclosure will be able to adapt its principles in light of what is known about extrusion or other forming arts to make alternative processes and devices that achieve the same end products as described herein. A scaled-up embodiment of this process may be adapted for use with, for example, a multi-zone screw extruder, with the solvent mixture provided via a suitable injector or a hopper and the zones controlled to provide a cold extrusion. Features such as the syringe pump can be replaced by a suitably metered and controlled liquid or solid polymer feed system The system has been used to make various products of porous solids, for example 6 F catheters with the properties shown in Table 1. Samples were made using 13% w/w 85 kDa PVA with either 0.1% w/w 450 k PAA or 1% w/w 20 k PVP-iodine. In all cases, samples were extruded into chilled ethanol between 0.degree. and 15.degree. C., soaked in ethanol overnight, then dried. Samples were then annealed in glycerol at 120.degree. C. between 6 and 17 hours, then rehydrated prior to testing. The samples were made with an average outer diameter of 1.59 mm (5 F) after a few days of hydration in aqueous solution and an average of 1.86 mm and 2.01 mm outer diameter for PVA-PAA and PVP-Iodine. These 6 F catheters were made with PVA. Tensile strengths for several of the formulations were evaluated at equilibrium water content (EWC), and showed an increased strength as compared to the ISO-10555 standard requirements could be readily obtained. These samples not only met, but exceeded ISO standards (see Table 1).

cycles in the samples they tested. The process of making these gels required multiple freeze-thaw cycles. The resultant materials were tested in a dry condition and are not comparable to strengths measured at EWC. Fukumori et al. reported that the crystalline content of the materials increased with the number of freeze-thaw cycles, and attributed the strength of the materials to large crystals being formed as the freeze-thaw cycles progressed, with the larger crystals forming superior crosslinks that increased the Tg of the materials. The nature of these processes produces a dried material. Moreover, as discussed below, a freeze-thaw process produces macropores.

In contrast, processes herein are free of freeze-thaw processes and/or free of a freezing process and/or free of a thawing process. Further the processes can be used to make solid porous materials that have little or no swelling, e.g., 0%-100% w/w swelling at EWC, even in an absence of covalent crosslinking agents Artisans will immediately appreciate that all ranges and values between the explicitly stated bounds are contemplated, with, e.g., any of the following being available as an upper or lower limit: 0, 5, 10, 15, 20, 25, 30, 40, 50, 60, 70, 80, 90, 95, 100% w/w, with swelling measured as % swelling=100.times.(Total weight at EWC–dry weight)/dry weight, with the dry weight being the weight of the material without water.

Figure 5:
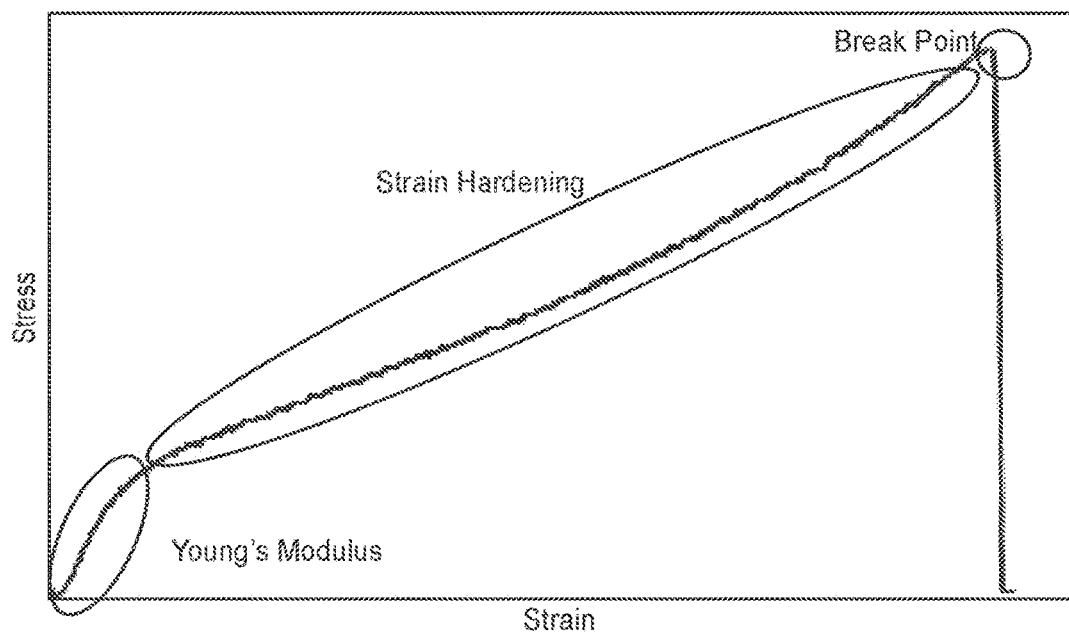
FIG. 5 is a plot depicting a stress-strain curve of a polymeric material.
Figure 6:
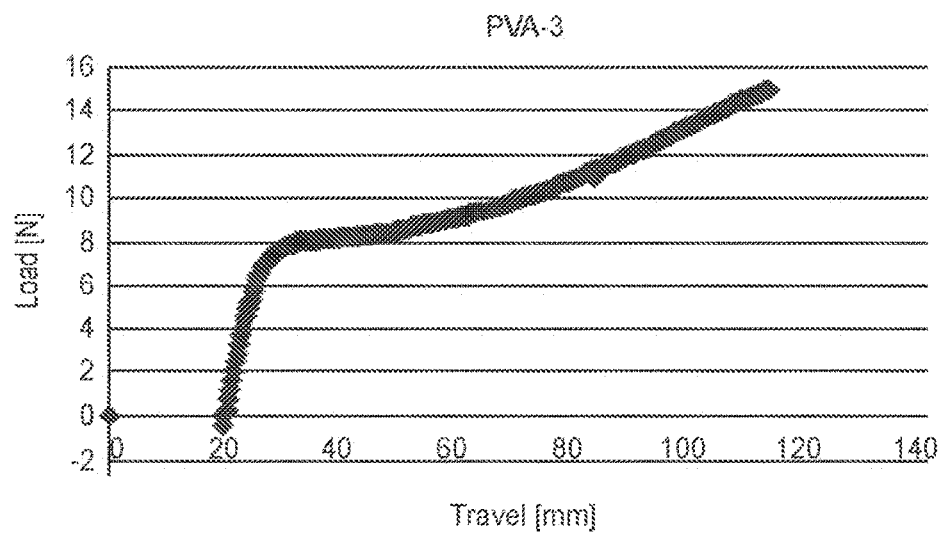
FIG. 6 is a plot of tensile test data for a porous solid made with the apparatus of FIG. 1.

FIG. 5 shows the different zones of a polymeric material stress-strain curve. There are three major zones: Young's Modulus, strain hardening, and break point. Young's Modulus is defined as the slope (change of stress/change of strain) of the linear elasticity of a material. Strain hardening is defined as the strengthening of a material due to deformation. Break point is the point of maximum elongation. Tensile load and travel were plotted for a PVA (5 F) sample as shown in FIG. 6. The shape of the load curve was representative of other samples which underwent tensile testing. The sharp initial slope and eventual leveling out as elongation occurs may indicate viscoelastic properties of the extruded PVA, where the material strain hardens and eventually undergoes strain softening until break. This particular sample exhibited a max tensile load of 14.9 N, with a travel

TABLE 1

| Sample | Avg. max tensile load [N] | % diff. ISO | Elongation at break | Young's modulus [N/mm$^2$] (MPa) | max stress [N/mm$^2$] (MPa) |
| --- | --- | --- | --- | --- | --- |
| PVA (5F), at EWC | 13.20 | +27.6% | 354% | 27.5 | 74.5 |
| PVA-PAA (6F), at EWC | 10.80 | +7.6% | 270% | 7.6 | 33.2 |
| PVP-Iodine (6F), at EWC | 11.35 | +12.6% | 268% | 12.57 | 24.4 |
| Fukumori (aGF-10), tested dry | Not reported | N/A | 6.3% | 8.9 | 180.6 |

Figure 7:
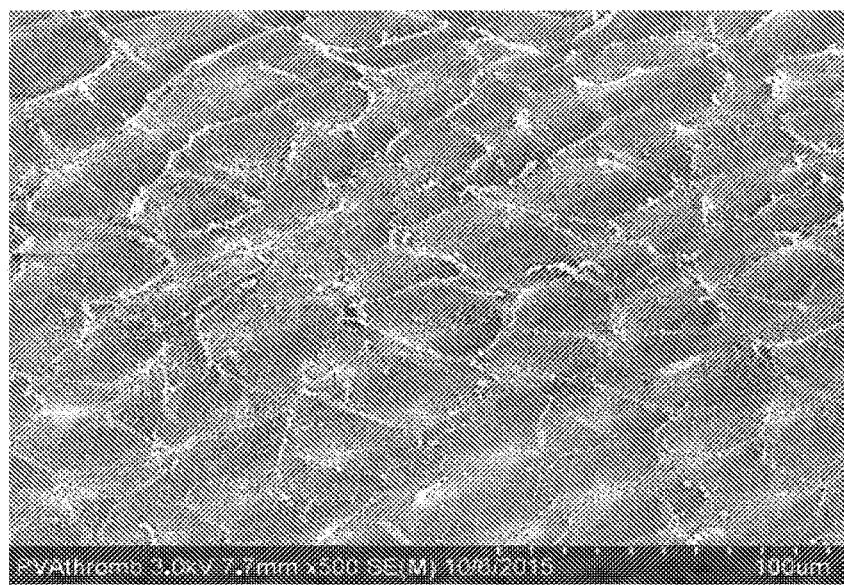
FIG. 7 is a scanning electron micrograph (SEM) of a surface of a porous solid.
Figure 8:
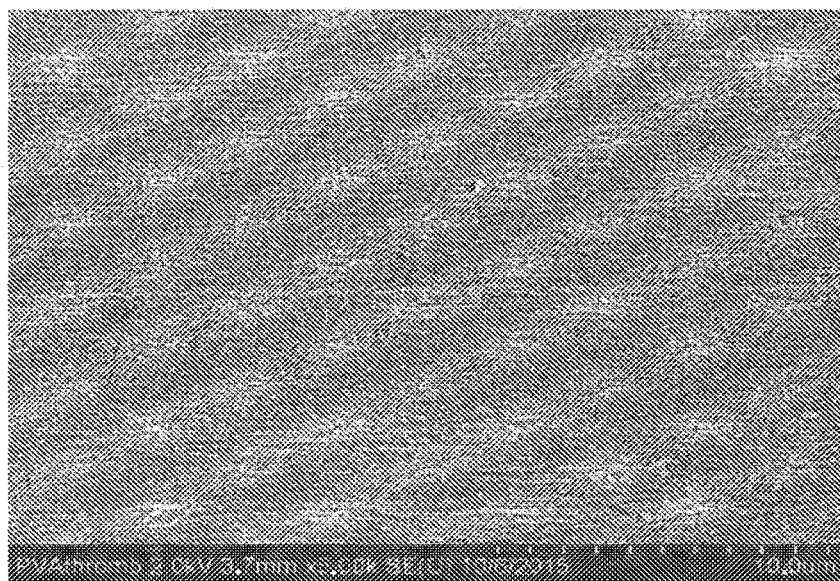
FIG. 8 is an SEM of a cross-section of the porous solid of FIG. 7.

The tensile results in Table 1 were obtained from one batch of samples. The minimum strength required by ISO 10555-1:2013 is 2.25 for catheters with an OD between 1.14 and 1.82 mm and 3.37 lbs (15 N) for catheters large than 1.82 mm. Average strength of samples created to using the finalized casting process (approximately 12 F) resulted in samples with tensile strength 164% greater than the required minimum tensile strength. Catheters and the like can be graded using the French nomenclature, which refers to an inner diameter in French (F) Fukumori et al. (2013), Open J. Organic Polymer Materials 3:110-116 reported a freeze-thaw process of making poly(vinyl alcohol) (PVA) materials with a Young's modulus of 181 MPa with a Young's modulus of about 5 MP or more requiring at least about 3 of 115 mm (454% elongation). Other samples made with the same process to have an average diameter of 2.03 (6.4 F) have an average maximum tensile strength of 24.6 N (5.52 lbs.). This substantial increase in tensile strength accompanying such a slight increase in cross-sectional area indicates that catheters made of these materials will greatly surpass ISO 10555 minimum standards. The extruded samples have a horizontal chain orientation and alignment along the length of samples (in direction of extrusion), as supported by the SEM of a nanoporous material provided in FIG. 7. A polymeric chain orientation produced by the extrusion process. FIG. 8 is an SEM image of cross-section of the same material prepared according to Example 1A indicating pore sizes of 100 nm or less.

The results in strength, radiopacity, and qualitative observations on surface finish and symmetry of the samples are very good. The sample surfaces were substantially, but not entirely, free of imperfections. No severe lines, bumps or other imperfections were observed, a result obtained with extrusion that is superior to the same ingredients when used to make casted samples which contained severe parting lines. Extrusion processes were observed to be efficient and useful for creating tough, high tensile strength tubing with high aspect ratios that are not possible using conventional molds. Drawing processes that are similar to the extrusion may also be employed.

Example 1A describes a general process for extruding a porous solid. Surprisingly, the process was effective. A cold extrusion process was created, with the die being kept on the extrusion side in the bath at only 13.degree. C. The polymer is hydrophilic and viscous at reduced temperatures. The cold extrusion was effective at making very strong materials with other good properties including smoothness, lack of defects, and consistent pore sizes. A mixture of a polymer in a solvent, with PVA in water being used in Example 1A, was used to achieve the extrusion. And extruding into a solvent-removing environment, which was an alcohol bath in this example, contributed to the desirable properties. In general, it is useful to have a combination of one or more of: extrusion of a hydrophilic polymer in a solvent; a cold extrusion, and extrusion into a bath that quickly removes solvent from the extrudate. Further, additional solvent-removing and/or annealing processes provide further utility for making desirable porous solids.

The process of Example 1A produced a nanoporous solid. Requirements for a nanoporous material include high polymer concentrations of more than about 10% w/w in the polymer-solvent mixture with high levels of crosslinking. Artisans will immediately appreciate that all ranges and values between the explicitly stated bounds are contemplated, with, e.g., any of the following being available as an upper or lower limit: 10, 12, 15, 16, 17, 18, 19, 20, 25, 30, 35, 40, 45, 50, 55, 60, 70, 80, 90, 95, 99% w/w of the polymer in the total weight of the polymer-solvent mixture. The polymer is to be substantially solvated, meaning it is a true solution or at least half the polymer is dissolved and the rest is at least suspended. The solvation of the polymer contributes to the alignment of the polymer chains in an extrusion and to crosslinking among the polymers. Without being bound to a particular theory, it is likely that high concentration of the starting polymer-solvent mixture help with this. And the probable chain alignment of the material as it passes through a die is thought to promote more intrapolymer versus interpolymer crosslinking. An extrudate or an otherwise formed mixture entering a desolvating environment, whether gas or liquid, is thought to further collapse pore structure before the densely concentrated polymer has completely crosslinked, thereby improving chain proximity and promoting additional crosslink density. Depositing the extruded or otherwise formed material directly into a solvent removing environment is helpful. Further solvent-removal can be continued to collapse the material until reaching a desired end point in structure and/or properties. An annealing process can further contribute to strength.

Frozen methods, on the other hand, rely on increased strengthening by forcing superconcentrated microregions to also achieve chain proximity and improve crosslink density, but retain a macro porosity due to the presence of ice crystals in the total gel structure. Desolvation creates forced superconcentrate microregions but these do not create macropores. In contrast, a pre-established gel prior to a dehydration or freezing is by nature of that process formed with macropores. Further, the work of the inventors indicates that such nanoporous solids have greater strength than macroporous materials.

Hydrogels can also be made by using a lower polymer concentration in the polymer-solvent mixture, generally less than 10% w/w of polymer in the polymer-solvent mixture. Artisans will immediately appreciate that all ranges and values between the explicitly stated bounds are contemplated, with, e.g., any of the following being available as an upper or lower limit: 2, 5, 7, 8, 9, 10% w/w of the polymer in the total weight of the polymer-solvent mixture. Further, or alternatively, the polymer-solvent mixture is not extruded into a solvent removing environment.

Microporous materials may be made with process conditions intermediate to nanoporous solids and hydrogels. One embodiment is to prepare a material using conditions comparable to making a nanoporous material but to stop solvent removal before solvent removal reaches a nanoporous solid structure.

Extrusion of hydrophilic polymers, including the PVA of Example 1A, in a solvent is helpful to make high strength materials. Use of a solvent in an extrusion starting material is, at the least, uncommon. Typically an extrusion uses a solid material that has been heated to a flowable temperature and then extruded, and later cooled by a variety of methods. For instance, it is believed that an extrusion of a pure PVA is possible. But such an extrusion would lack the polymeric structure that is needed to make porous solids and would instead behave like a conventional plastic. According to a theory of operation, a pure PVA extrusion would lack the quality of hydrogen bonding that takes place in an aqueous ionic solvent state. A temperature suitable for preparing the PVA to be flowable in an extrusion would create a poorly cohesive material at the die head so that a continuous shape does not form. It was difficult to make extruded PVAs to form high aspect shapes, e.g., tubes, and to use them in an extrusion process. Viscosities of PVA and other hydrophilic polymers are high, and difficult to get into solution. It was observed that a narrow working band of temperature was useful, e.g., 85-95.degree. C. Below about 85.degree. C., PVA failed to truly melt, and thus did not become completely amorphous for extrusion. Above about 95.degree. C., losses to boiling and evaporation made the process ineffective. These temperature ranges could be offset by increasing pressure above atmospheric, but a pressurized system is challenging to use and to scale. The processes are usefully performed at a temperature below a boiling point of the polymer-solvent materials.

The cohesive strength of the flowing polymer-solvent mixture was weak when exiting the die. The use of a core to support the mixture at the die is useful to hold the shape at the die. This condition is in contrast to a typical core extrusion used as a coating process, e.g., for coating wires for a mobile telephone charger. A typical process that avoid use of a solvent or a significant solvent concentration has a relatively higher cohesive strength that it exits the die that is readily capable of holding a tube, and do not relying on active bonding such as the hydrogen bonding in hydrophilic polymers that form the solid material in a coherent shape as it moves out of the die.

Passing the formed polymer-solvent mixture into solvent removal environment was useful. In Example 1A, for instance, using a cold ethanol bath is atypical relative to a conventional extrusion. Most extrusions do not use bath temperatures at or below room temperature. Moreover, the use of a solvent removing bath is a typical relative to conventional processes the bath or other solvent removing environment helps solidify the extruded material sufficiently that it remains stable and concentric on the core, otherwise the melt would run into a tear drop shape. It would also be destroyed in the attempt to collect it at the end of the extrusion as it would still be molten. Conventional baths containing water would cause the PVA or similar hydrophilic polymer material to lose shape due to swelling, dissolution, or both. Example 1B is directed to molding processes that involve preparation of a polymer-solvent mixture that is formed in a mold and then processed into a solvent-removing environment. These processes do not have the advantages of alignment of chains observed in an extrusion. However a suitably controlled temperature and solvent removal can yield materials with a high strength and controlled pore structure.

Figure 9:
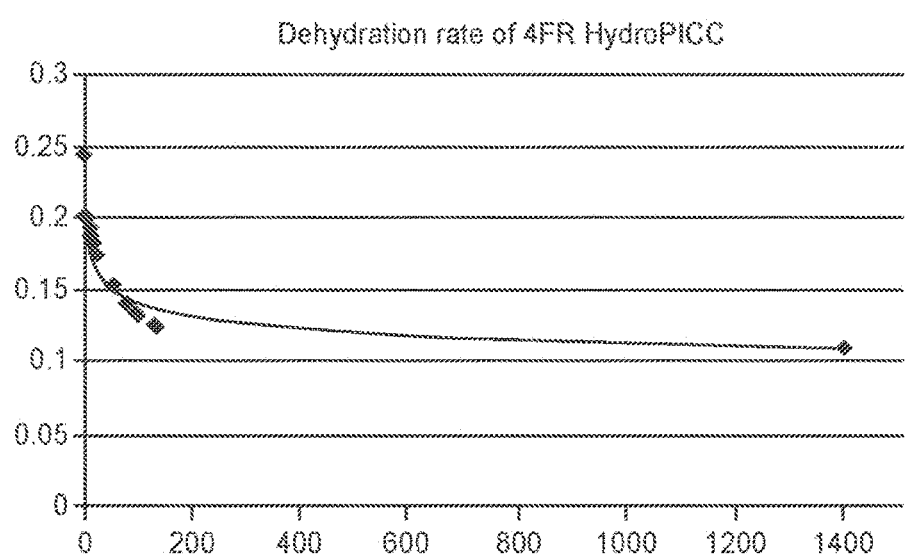
FIG. 9 is a plot of data for dehydration of a porous solid catheter, with the y-axis being weight and the x-axis being time in minutes.

Example 2 demonstrated the process was effective when it incorporated a radiopaque additive, with barium sulfate being the material used in this instance. In Example 3, the porous materials, when exposed to air at ambient conditions, lost water (FIG. 9) but retained their desirable properties and can be effectively transported stored in sealed packages or in solution, or left in ambient conditions for a reasonable storage duration or as may be needed after being unpackaged by a user for an end-use. Example 4, demonstrates strength (modulus and ultimate break) increased as the hydrophilic polymer (PVA) molecular weight was increased from 140 k to 190 k (Table 3). Bismuth subcarbonate was used as a radioopaque agent. In the same Example, an increase in a concentration of the polymer in the polymer mixture used for extrusion showed an increase in strength for the highest concentration relative to the lower concentration (Table 5 and FIGS. 10-11).

The porous solids are highly lubricious and can be used in a hydrated state and can be conveniently bonded to other materials. In the case of a catheter, for instance, extensions, luer locks, suture wings, and the like are useful. Example 5 demonstrates that conventional processes are effective in bonding other materials to the porous materials. Examples 6 and 7 showed that the porous solids were suitable for radioopaque medical devices and had good burst strengths in pressure tests. Contact drop testing (Example 8) showed that various porous solids were hydrophilic (PVA tested). SEM images (FIGS. 15A-15B, Example 8) are images of a nanoporous solid. Example 9 is directed to a nanoporous solid (FIGS. 16A-16D).

Observations of the tested samples indicated that, without being limited to a particular theory, crosslinks within the material provided by a first hydrophilic polymer (PVA) were increased by interaction with the chains of a second polymer (PAA or PEG) until the second polymer began to form domains with itself in the material. This is likely due to the ability to incorporate higher molecular weight species of the second polymer (PAA or PEG) providing additional material strength. The results generally indicate that copolymer extrusion is useful in ranges of the second polymer from 0.1% to 10% w/w or no more than 10% w/w of the first polymer, with no more than 5% w/w also being useful. Artisans will immediately appreciate that all ranges and values between the explicitly stated bounds are contemplated, with, e.g., any of the following being available as an upper or lower limit: 0.1, 0.2, 0.4, 0.5, 0.8, 1, 2, 3, 4, 5, 6, 8, 10% w/w.

Figure 17A:
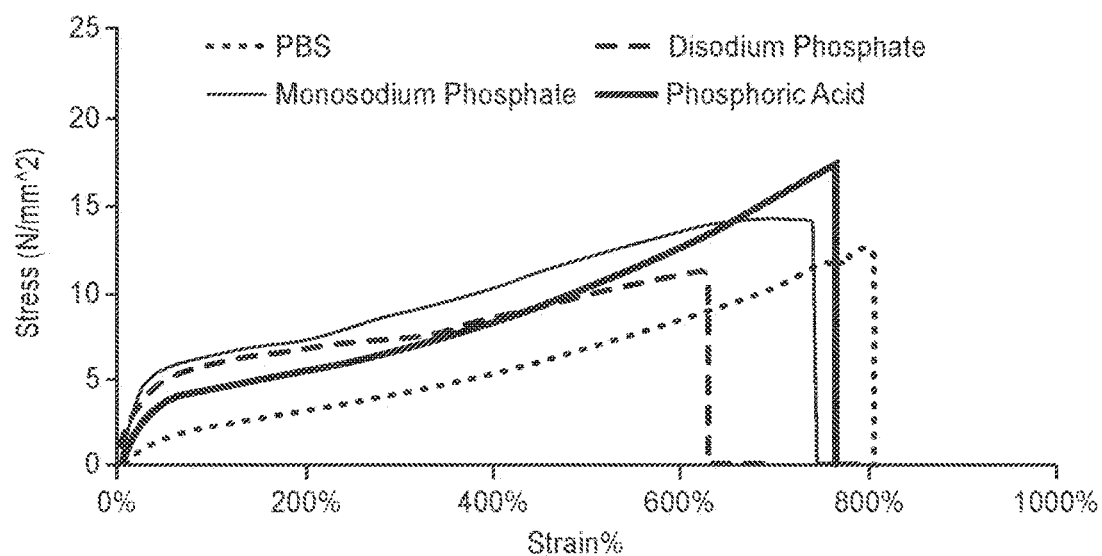
FIGS. 17A-17B are plots of tensile test data for samples generated as described in Example 10.
Figure 17B:
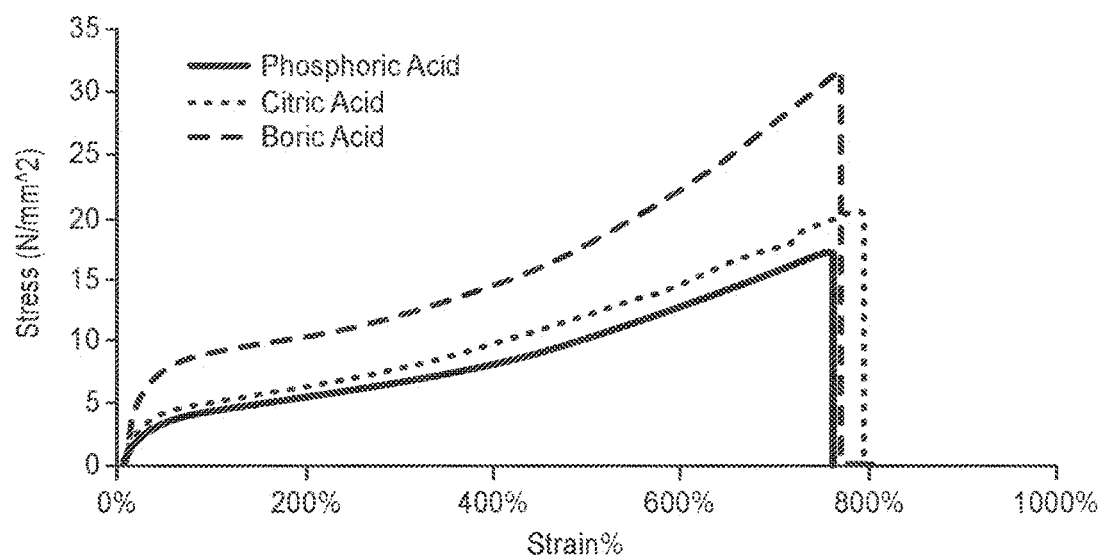

The effects of various salts on properties of the porous solids were assessed as described in Example 10 (FIGS. 17A-17B). Salts were useful to manipulate the strength of the materials. Without being limited to a particular theory, it is likely the salts were part of the physical crosslinking, in effect acting as small molecular weight crosslinkers between the polymer chains. Monosodium phosphate resulted in the highest Young's Modulus and phosphoric acid produced the highest tensile. Boric acid increased both Young's Modulus and maximum tensile stress, whereas citric acid and phosphoric acid were comparable to each other. Boric acid forms high strength crosslinks but is not a covalent crosslinker.

Figure 12:
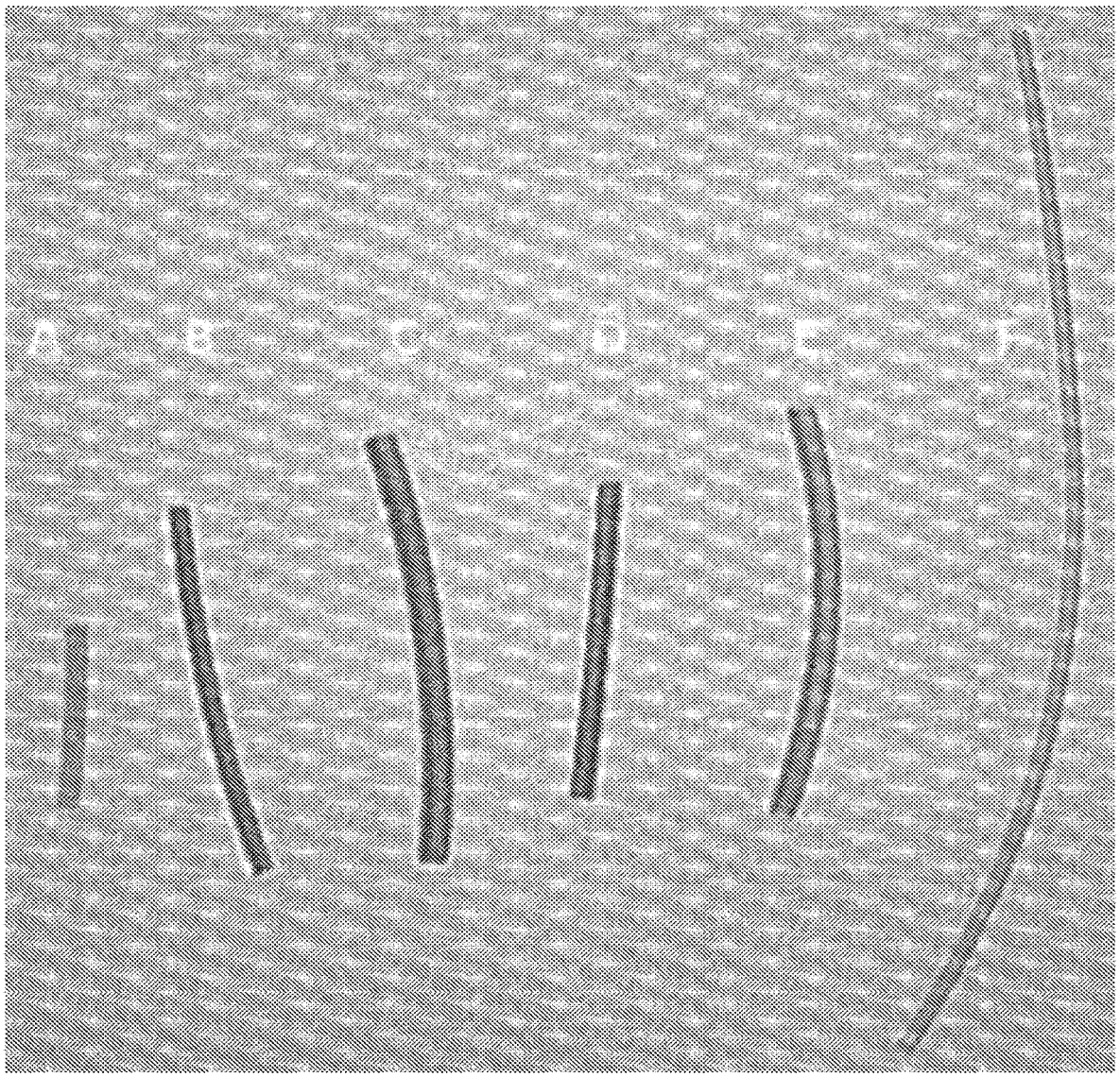
FIGS. 12A-12F are photographs of porous solids that incorporate a radioopaque agent: 12A, control (Bard POWERPICC), 12B, 5.7% bismuth subcarbonate by weight, not annealed, 12C, 12.1% bismuth subcarbonate by weight, not annealed, 12D, 12.1% bismuth subcarbonate by weight, annealed, 12E, 5.7% bismuth subcarbonate by weight, annealed, 12F, 4.2% bismuth subcarbonate by weight.
Figure 18A:
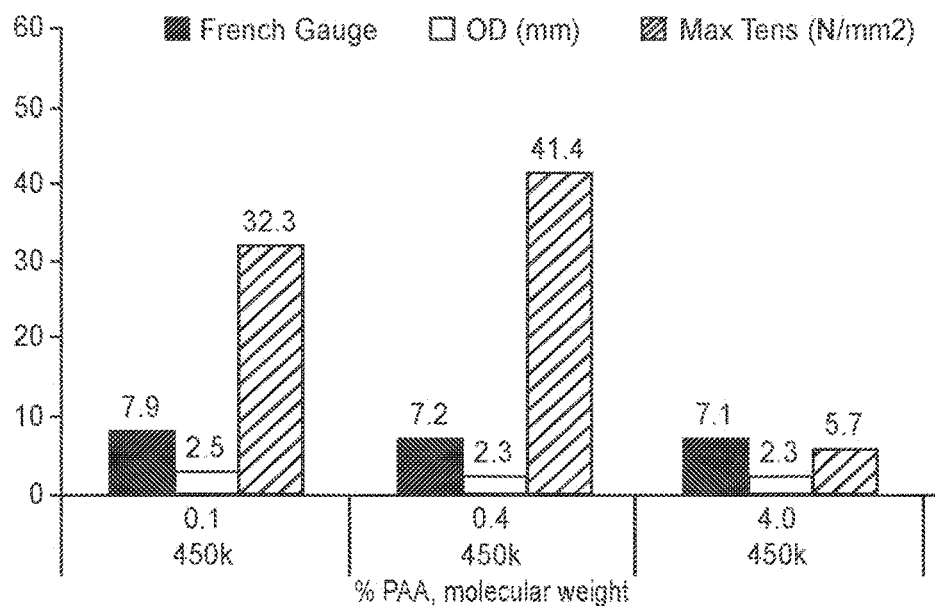
FIGS. 18A-18B are plots of tensile data for various blends of polymers described in Example 11, with data being shown in N/mm·sup.2.

Further tensile tests were performed for coextrudates with a concentration of a first hydrophilic polymer and a relatively lower concentration of a second hydrophilic partner, Example 11. FIG. 18A depicts tensile test for a PVA mixture having a low concentration of 450 kDa PAA (0.1, 0.4, or 4.0% w/w PAA, 16% w/w PVA, percentages are polymer w/w concentration in solvent). The 0.1-0.4% w/w PAA concentrations had a higher strength and support the conclusion described for Examples 9 and 10, above. A higher molecular weight (MW) PAA (3 million Da) was tested (FIG. 18B) but generally had only about half the strength of the lower MW PAA. The decrease in tensile strength with increased PAA molecular weight may be due to decreased bonding and/or tangling interactions between PVA and PAA due to the longer 3 million MW chains. No significant differences in strength were observed when three different MWs of PEGs were blended with PVA (8 k, 20 k, 35 k PEGs, FIGS. 19 and 20A-20C, Example 12). Porous plastics made of PVA without a radioopaque agent were superior to control catheters in regards to non-thrombogenicity (Example 13, FIGS. 21A-12B).

Embodiments for polymer blends include at least one first hydrophilic polymer and at least one second hydrophilic polymer in a solvent that is extruded as described herein. Examples include combinations of one or more of PVA, PAA, PEG, PVP, polyalkyenes, a hydrophilic polymer, and combinations thereof. Examples of concentrations include the at least one second hydrophilic polymer being present at 1 parts to 10,000 parts of the first hydrophilic polymer. Artisans will immediately appreciate that all ranges and values between the explicitly stated bounds are contemplated, with, e.g., any of the following being available as an upper or lower limit: 1, 2, 10, 100, 1000, 1500, 2000, 2500, 3000, 4000, 5000, 6000, 7000, 8000, 9000, 10000 parts. Examples of concentrations of polymers in a polymer-solvent mixture include a first polymer present at a first: concentration and one or more further polymers present at a second concentration, with the first polymer concentration and the further polymer concentration being independently selected from 0.1-99%, e.g., 0.1, 0.2, 0.3, 0.4, 0.5, 0.6, 1, 2, 3, 4, 5, 6, 7, 8, 9, 10, 11, 12, 13, 14, 15, 16, 17, 18, 19, 20, 25, 30, 33, 35, 40, 45, 50 55, 60, 65, 70, 75, 80, 85, 90, 95% w/w. Further, non-hydrophilic polymers and/or non-hydrophilic blocks in block polymers, may be present, with concentrations of such polymers and/or such blocks generally being less than about 10% w/w, e.g., 0.1, 0.2, 1, 2, 3, 4, 5, 6, 7, 8, 9, 10% w/w.

Processing Systems and Parameters to Make Materials

Processes are provided herein to create biocompatible porous solids such as microporous or nanoporous solid materials that possess low protein adsorption properties and provide a basis for non-biofouling devices. Modification of starting polymer concentration, molecular weight, solvent removal, forming processes, and hardening/annealing processes may be utilized to provide surface properties with reduced protein adsorption and other properties. Certain embodiments include creation of various continuous shapes through extrusion of a polymeric mixture. The mixture may be further hardened and annealed. These processes may be used to create a tough and highly lubricious material. Embodiments include polymeric mixtures extruded into shapes possessing single or multiple lumens, of varied diameters and wall thickness.

An embodiment of a process for making a nanoporous solid material comprises heating a mixture that comprises a polymer and a solvent (a polymeric mixture), extruding the mixture into a solvent-removing environment, and removing the solvent from the crosslinked matrix until a nanoporous solid material is formed. One or more of these actions may be combined, depending on the process. Further, cooling the mixture as it passes out of the die is useful. Without being bound to a specific theory of operation, it appears that crosslinking the polymer during passage through the die initially forms a porous matrix that is not a true nanoporous solid material because, although it has spaces between polymer strands, it does not have a pore-structure. As the solvent is removed under appropriate conditions, the crosslinked structure becomes a nanoporous solid. The crosslinking starts when the polymeric mixture is extruded through a die, and as the mixture is cooled. The crosslinking may continue while the solvent is removed. The transition to form the nanoporous material takes place as the solvent is removed and, in general, is believed to be completed or essentially completed (meaning 90% or more) at this stage. The resultant material may be further processed by annealing with or without a presence of further solvents, or plasticizers. This process, and the other extrusion or other formation processes and/or materials set forth herein, may be free of one or more of: covalent crosslinking agents, agents that promote covalent crosslinks, radiation that crosslinks polymer chains, freezing, thawing, freeze-thaw cycles, more than one freeze-thaw cycle, ice-crystal formation, foaming agents, surfactants, hydrophobic polymers, hydrophobic polymer segments, reinforcing materials, wires, braids, non-porous solids, and fibers.

The porous materials may be made by an extrusion process comprises passing a polymeric mixture through a die into a cooling environment. The cooling environment may further be a solvent-removing environment. It is a dehydrating environment when the solvent is water. The die may have a core that passes through it so that the polymeric mixture may be formed around the core. Further solvent-removal environments and/or annealing environments may be used.

The extrusion process for a polymer-solvent mixture may be performed as a cold extrusion. The term cold extrusion refers to a process that involves passing a polymer-solvent mixture through a die and does not require heating the polymer-solvent mixture above its boiling point during the entire process of preparing the polymer-solvent mixture and extruding it. Accordingly, in a cold extrusion, the die head is kept below a boiling point of the polymer-solvent mixture. Although many solvents may be used, water is often a useful solvent in which case the die head is kept at 100.degree. C. or less, although colder temperatures may be useful, as discussed above. The term polymeric mixture refers to a polymer that is in solution, dissolved, or suspended in a solvent. A solvent may be, e.g., water, aqueous solution, or an organic solvent. Heating the polymeric mixture may comprise heating the mixture to a temperature above the melting point of the polymer. In general, the solution transitions from a cloudy to a clear state when it reaches the melt point.

Extrusion is a useful process for forming the materials. Other forming processes may be used, for example, molding, casting, or thermal forming polymer-solvent mixtures. In general, a polymer-solvent mixture is prepared without boiling and formed into a shape that is exposed to solvent-removal conditions that are controlled to make a nanoporous or macroporous material using the guidance provided herein. An annealing process may be included. Hydrogels that are not microporous or nanoporous materials can also be made.

The heated polymeric mixture may be molded or otherwise formed as it is cooled or molded/formed and immediately cooled. Formed is a broad term that refers to passing the material from an amorphous melted state into an end-user product or an intermediate shape for further processing. Forming encompasses casting, layering, coating, injection molding, drawing, and extrusion. The forming can be done using an injection molding set up, where the mold consists of a material with thermoconductive properties allowing it to be heated easily to enhance the flow of the injected polymeric mixture, and to be cooled rapidly in a cooling environment. In other embodiments, the molding process can be accomplished by extrusion of the polymeric mixture through a die to form continuous material.

Cooling the polymeric mixture may comprise, e.g., cooling an extruded material, as in the case of passing the polymeric material through a die. An embodiment for cooling is a liquid bath at a temperature at least 20.degree. C. cooler than the polymeric mixture boiling point or alternatively below the polymeric mixture Tm, e.g., 20, 30, 40, 50, 60, 70, 80, 90, 100, 110.degree. C. below the boiling point or polymeric Tm, or alternatively the bath or other environment being at a temperature from −50 to 30.degree. C.; Artisans will immediately appreciate that all ranges and values between the explicitly stated bounds are contemplated, with, e.g., any of the following being available as an upper or lower limit −50, −45, −25, −20, −10, −5, −4, 0, 15, 20, 25, 30.degree. C. The cooling may be performed in a solvent removing environment. Freezing temperatures may be avoided. Without being bound to a particular theory of operation, the polymer chains are cooled to the point of promoting crosslinking and immobilizing chain movement. This may occur at temperatures as high as 30.degree. C., or higher if time is allowed. The bath may be aqueous, and, by adjustment with salt or other osmotic agents, may be provided at an osmotic value to perform solvent removal on aqueous materials that are at a relatively lower osmotic value through osmotic pressure and diffusion. The bath may also be other solvents that freeze at temperatures lower than water, so that temperatures below 0.degree. C. may be used without freezing the solvent or materials. In the event that hydrophilic copolymers are used in conjunction with PVA, for instance, temperatures higher than 20.degree. C. may be used as crosslinking and chain immobilization will occur at much higher temperatures.

A solvent-removing environment refers to an environment that, significantly accelerates removal of a solvent as compared to drying at ambient conditions. Such an environment may be non-heating, meaning it is not above ambient temperature, e.g., not above 20.degree. C. Such an environment may be a vacuum, e.g., a vacuum chamber, a salt bath, or a bath that removes the solvent in the polymeric mixture. For instance, an aqueous polymeric mixture may be introduced into an ethanol bath, with the ethanol replacing the water. The ethanol may subsequently be removed. A salt bath may be, e.g., a high salt concentration bath (1M to 6M). A time of processing in a solvent-removing environment and/or a cooling process may be independently chosen to be from 1 to 240 hours; Artisans will immediately appreciate that all ranges and values between the explicitly stated bounds are contemplated, with, e.g., any of the following being available as an upper or lower limit: 1, 2, 5, 10, 24 hours, 1, 2, 5, 7, 10 days. Salts may be salts that dissociate to make single, double, or triply charged ions.

One or a plurality of solvent-removing environments may be used, or one environment may be adjusted with respect to temperature. Thus a cooling bath may be used followed by solvent removal in an oven or vacuum oven. A washing step may be performed before or after cooling or solvent removal, e.g., by soaking in a series of solvents of varying concentrations, varying salt solutions, varying proportions of ethanol or other solvents.

An embodiment is an extruded material that has been through a solvent-removal process comprising exposure to a salt bath, the material being is soaked in a series of diH20 baths (new baths or exchanged) for a period of time (e.g., 2-48 hours, 4-24 hours) to remove excess salt from the cast material or end-user device. The material is removed from the wash step, and dehydrated to remove excess water. Dehydration can be done using, e.g., temperatures ranging from 20-60.degree. C. Dehydration is generally performed at 37.degree. C. for greater than 24 hours.

An embodiment is a polymeric mixture that has been extruded or otherwise formed that is then exposed to a high salt concentration bath (1M to 6M) for an inversely correlated period of time; high salt reduces the time required for soaking; for instance, it is soaked for 16-24 hours in a 6M solution of NaCl. After soaking, the material is rinsed free of salt solution. The material is now toughened and can be removed from any mold pieces carried over from the initial formation. Alternatively, after a salt or other bath, the material is soaked in water baths and dehydrated to remove excess water. Dehydration can be done using temps ranging from 20-60.degree. C. Dehydration may be performed at 37.degree. C. for greater than 4 hours, greater than 24 hours, or in a range from 4 to 150 hours; Artisans will immediately appreciate that all ranges and values between the explicitly stated bounds are contemplated, with, e.g., any of the following being available as an upper or lower limit: 4, 6, 8, 10, 12, 16, 24, 48, 72, 96, 120, 144, 150 hours. For instance, dehydration at 40.degree. C. for 6-24 hours has been observed to be useful.

In another embodiment, NaCl is incorporated into the starting polymeric solution at concentrations ranging from 0.1 to 3M of the final polymeric mixture volume. A polymer is dissolved in a heated solution under agitation, then brought above its melt point. To this solution, dry NaCl is added slowly under agitation until completely dissolved. The slightly hazy solution is then drawn into a feed for the purpose of creating a shape, either through injection molding, casting, extrusion and/or drawing. A quench is performed at the end of each process to rapidly reduce the temperature and form a solid material. In this embodiment, no additional salt soak is required. After material hardening, if necessary, the material is removed from any molding process parts and rinsed in water to remove salt and dehydrated.

The term annealing, as used in the context of a semi-crystalline polymer or a solid porous material refers to a heat treatment at an annealing temperature comparable to the melting temperature of the polymer or the polymers in the nanoporous material. This temperature is usually less than, and is within about 0-15% of, the melting temperature. Plasticizers or other materials may affect the melting temperature, usually by depressing it. For a pure PVA, for instance, the annealing temperature will be within about 10% of the melting point of the PVA; with other materials present, the annealing temperature will typically be lower. A theory of operation is that the annealing is a process that is a relaxation of stress combined with increase in the size of crystalline regions in the material being annealed. Unlike metals, annealing increases the strength of the annealed material. Annealing may be performed in one or more of: in air or in a gas or in an absence of oxygen or an absence of water, e.g., in nitrogen, in vacuum nitrogen, under argon, with oxygen scavengers, and so forth. For example, experiments have been made with annealing dehydrated PVA nanoporous materials. Annealing is utilized to increase crystallinity in the PVA network, further reducing pore sizes of the PVA network and to reduce adsorption properties of the final gel surface. Annealing can be done at temperatures ranging from, e.g., 100-160.degree. C.; in a preferred embodiment, this step is performed submerging the dehydrated gel into a bath of mineral oil.

Annealing may be performed in a gas or a liquid at ambient, elevated, or low (vacuum) pressure. The liquid may be a low molecular weight polymer (up to 2000 Da) or other material (e.g., mineral oil). Examples of low molecular weight polymers are: glycerin, polyols, and polyethylene glycols of less than 500 MW. A useful embodiment is annealing in a bath of glycerin at, e.g., 140.degree. C. for 1-3 hours; glycerin acts to further reduce fouling properties of the gel through interaction and neutralization of the free hydroxyl end groups of the PVA network. The annealed nanoporous material is allowed to cool, removed from the annealing bath and rinsed free of bath medium using a series of extended soaks. The product is then dehydrated to prepare for terminal sterilization.

Various types of dies may be used, e.g., longitudinal, angular, transverse and spiral extrusion heads, as well as single-polymer extrusion heads used for extruding a single polymer and multi layers extrusion heads used for simultaneous extrusion of a plurality of polymer layers or other layers. Continuous operation heads may be used, as well as cyclical. Various materials may be incorporated into, or as, a layer: for example, a reinforcing material, a fiber, a wire, a braided material, braided wire, braided plastic fibers, and so forth. Similarly, such materials may be excluded. Moreover, the porous solid may be made with a certain property, e.g., Young's modulus, tensile strength, solids content, polymer composition, porous structure, or solvent content that is known and thus measureable exclusive of various other materials. Accordingly, embodiments include materials disclosed herein that are described in terms of the materials' properties without regard to various other incorporated materials. For instance, a nanoporous solid has a certain Young's modulus that is known even if the material has a reinforcing wire that contributes further strength A core may be used with an extrusion die. The core may be air, water, a liquid, a solid, a non-solvent or a gas. Artisans reading this disclosure will appreciate that various extrusion processes using these various kinds of cores may be use. Cores made of polytetrafluoroethylene, tubing (PTFE) are useful.

Multi lumen tubing has multiple channels running through its profile. These extrusions can be custom engineered to meet device designs. Multi Lumen tubing has a variable Outer Diameter (OD), numerous custom Inner Diameters (ID's), and various wall thicknesses. This tubing is available in a number shapes; circular, oval, triangular, square, and crescent. These lumens can be used for guidewires, fluids, gases, wires, and various other needs. The number of lumens in multi lumen tubing is only limited by the size of the OD. In certain embodiments, OD's are as large as 0.5 in., ID's can be as small as 0.002 in., and web and wall thicknesses can be as thin as 0.002 in. Tight tolerances can be maintained to +/−0.0005 in. Artisans will immediately appreciate that all ranges and values between the explicitly stated bounds are contemplated, with, e.g., any of the following being available as an upper or lower limit for an OD and/or ID: 0.002, 0.003, 0.004, 0.007, 0.01, 0.02, 0.03, 0.04, 0.05, 0.1, 0.2, 0.3, 0.4, and 0.5 in. Tolerances may be, e.g., from 0.0005 to 0.1 in.; Artisans will immediately appreciate that all ranges and values between the explicitly stated bounds are contemplated, with, e.g., any of the following being available as an upper or lower limit: 0.0005, 0.001, 0.002, 0.003, 0.006, 0.01, 0.02, 0.03, 0.06, 0.8, 0.9, 1 in.

Braid reinforced tubing can be made in various configurations. For instance, it is possible to braid using round or flat, single or double ended wires as small as 0.001 in. Various materials can be used to make the braided reinforced tubing including stainless steel, beryllium copper, and silver, as well as monofilament polymers. The braid can be wound with various pies per inch over many thermoplastic substrates such as nylons or polyurethanes. The benefits of braided catheter shaft are its high torque-ability and kink resistance. By changing several factors during the braiding process, the characteristics of the tube can be altered to fit performance requirements. After braiding is complete, a second extrusion may be applied on top of the braided tube to encapsulate the braid and provide a smooth finish. Walls as thin as 0.007 in. can be achieved when a braid reinforced tube is required.

Porous, Microporous, and Nanoporous Materials

Porous solid is a term used broadly herein to refer to materials having a solid phase containing open spaces, and is used to describe true porous materials and also hydrogels having an open matrix structure. Some terms related to porosity are used somewhat loosely in scientific literature such that it is helpful to provide certain definitions herein. The term nanoporous material or nanoporous solid is used herein to specifically refer to a solid made with interconnected pores having a pore size of up to about 100 nm diameter. The term diameter is broad and encompasses pores of any shape, as is customary in these arts. The term microporous solid or microporous material is similarly used herein to specifically refer to a solid made with interconnected pores having a pore size of up to about 10 .mu.m diameter. These nano- or micro-porous materials are characterized by an interconnected porous structure. Some hydrogels, which artisans sometimes refer to as hydrogel sponges, are also true porous materials that have a continuous and solid network material filled through voids, with the voids being the pores. However, an open matrix structure found in many hydrogels is not a true porous structure and, in general, while it is convenient to refer to them as porous materials, or to use analogies to pores when characterizing diffusive or other properties, such hydrogels are not nanoporous or microporous solids as those terms are used herein. The spaces between strands of an open matrix hydrogel, and the strands of the matrix are not interconnected pores. Hydrogels are crosslinked gels that have solid-like properties without being a true solid although it is convenient herein and generally in these arts to refer to them as a solid because they are crosslinked, insoluble in solvent, and have significant mechanical strength. Hydrogels may have a high water content, e.g., 25% w/w at EWC or more. Artisans in the hydrogel arts sometimes use the term porous, to characterize a net molecular weight cut off or to refer to spacing between strands of an open hydrogel matrix, in which case the hydrogel does not have a true porous structure and is not a nanoporous or a microporous material as those terms are used herein. The definitions of nanoporous material and microporous material as used herein also contrast with a convention that is sometimes followed wherein microporous substances are described as having pore diameters of less than 2 nm, macroporous substances have pore diameters of greater than 50 nm, and a mesoporous category lies in the middle.

The extrusion process for making the inventive materials has some advantages. The extrusion has been observed to align the polymers to a parallel orientation that contributes to high tensile strength. Having been extruded and stretched, the polymer molecules become aligned in the direction of the tube or fiber. Any tendency to return to a random orientation is prevented by the strong intermolecular forces between the molecules. Further, extrusion provides for creation of materials or devices with a high aspect ratio as compared to injection molding or other molding processes. Moreover, extrusion provides good control of dimensions such that wall thickness, placement of the lumen or lumens can be controlled. The use of high concentrations of polymers, above their melt point, in a solvent was useful for enabling extrusion. It is significant that attempts by others to use similar polymers to make high strength materials used other techniques that do not allow for extrusion, that are less efficient, and often unsuited for making actual end-user products.

For example, poly(vinyl alcohol) (PVA) was used herein to make nanoporous materials with excellent properties, especially as compared to conventionally used PVA medical materials. In fact, PVA has been used extensively throughout the medical device industry with a well-established track record of biocompatibility. PVA is a linear molecule with an extensive history as a biocompatible biomaterial. PVA hydrogels and membranes have been developed for biomedical applications such as contact lenses, artificial pancreases, hemodialysis, and synthetic vitreous humor, as well as for implantable medical materials to replace cartilage and meniscus tissues. It is an attractive material for these applications because of its biocompatibility and low protein adsorption properties resulting in low cell adhesion compared with other hydrogels.

Others have tried to improve the properties of PVA for biomedical purposes. For instance, others have experimented with a freeze/thaw processes. And techniques for formation of hydrogels from PVA such as "salting out" gelation have been shown to form useful polymer hydrogels using different molecular weights and concentrations. Manipulation of Flory interactions has also been studied in the formation of PVA gels through the combination of two solutions (see U.S. Pat. Nos. 7,845,670, 8,637,063, 7,619, 009) for the use of PVA as an injectable in situ forming gel for repairing intervertebral disks. In general, prior processes for fabricating tough PVA materials were studied in U.S. Pat. No. 8,541,484. Methods for doing so without the use of radiation or chemical crosslinkers have also been previously studied, as shown in U.S. Pat. No. 6,231,605. None of this PVA-related work by others has resulted in the inventions that are set forth herein. Some of these other materials were useful in regards to tensile strength but were nonetheless macroporous in nature.

In contrast, processes herein provide high strength materials with a true porous structure and other useful characteristics such as an unexpectedly good combination of biocompatibility and mechanical properties. Embodiments of porous solid materials are provided that have a combination of structural features independently chosen from pore sizes, tensile strength, Young's modulus, solids concentration, crosslinking type and degree, internal alignment, hydrophilicity, and composition for the materials and further, optionally, independently selecting end-user devices or intermediate materials having a desired aspect ratio for molded shapes, a lumen, a plurality of lumens, tubes with concentrically placed lumens or a range of tolerance of thickness, or a particular medical device: each of these are further detailed herein.

Embodiments include nanoporous materials with pore diameters of 100 nm or less, or within a range of 10-100 nm; Artisans will immediately appreciate that all ranges and values between the explicitly stated bounds are contemplated, with, e.g., any of the following being available as an upper or lower limit: 1, 2, 3, 4, 5, 10, 20, 50, 60, 70 80, 90, 100 nm.

Embodiments include nanoporous materials or microporous materials with a tensile strength at break of at least about 50 MPa or from 1-300 MPa measured at EWC. Artisans will immediately appreciate that all ranges and values between the explicitly stated bounds are contemplated, with, e.g., any of the following being available as an upper or lower limit: 10, 20, 30, 40, 50, 60, 70, 100, 200, 300 MPa.

Embodiments include nanoporous materials or microporous materials with a Young's modulus strength of at least about 1 MPa or from 1-100 MPa measured at EWC. Artisans will immediately appreciate that all ranges and values between the explicitly stated bounds are contemplated, with, e.g., any of the following being available as an upper or lower limit: 5, 10, 15, 20, 25, 30, 35, 40, 50, 60, 70, 80, 90, 100 MPa.

Embodiments include nanoporous materials or microporous materials or hydrogels with an elongation at break of at least about 100% or from 50-500% measured at EWC. Artisans will immediately appreciate that all ranges and values between the explicitly stated bounds are contemplated, with, e.g., any of the following being available as an upper or lower limit: 50, 60, 70, 80, 90, 100, 200, 300, 400, 450, or 500%.

Embodiments include nanoporous materials or microporous materials or hydrogels with a solids content of at least 20% or solids from 20-90% w/w measured at EWC; Artisans will immediately appreciate that all ranges and values between the explicitly stated bounds are contemplated, with, e.g., any of the following being available as an upper or lower limit: 5, 10, 25, 30, 35, 40, 45, 50, 55, 60, 65, 70, 80, 90% w/w percent solids. Percent solids are measured by comparing a total weight at EWC to dry weight.

The tensile strength, modulus, and elongation values may be mixed-and-matched in combinations within the ranges as guided by this disclosure.

Embodiments include nanoporous materials or microporous materials or hydrogels with physical crosslinks or covalent crosslinks or a combination thereof. Physical crosslinks are non-covalent, e.g., physical crosslinks are ionic bonds, hydrogen bonds, electrostatic bonds, Van Der Waals forces, or hydrophobic packing. The materials may be made free of covalent crosslinks, covalent crosslinkers and chemical products thereof. Chemicals can be added during processing to create covalent crosslinks, as is known in the arts of polymerization. Alternatively, the processes and materials may be free of the same.

Embodiments include nanoporous materials or microporous materials or hydrogels with an internal alignment of the polymeric structure. Alignment may be visualized using SEM images in sections taken along the direction of extrusion, i.e., longitudinally for a tube. Alignment refers to a majority horizontal chain orientation and along the length of samples (in direction of extrusion).

Embodiments include nanoporous materials or microporous materials or hydrogels with a hydrophilic surface and/or material. Materials made from polymers that are water soluble are hydrophilic. A water soluble polymer is a polymer that is soluble in water at a concentration of at least 1 g/100 ml. A surface is hydrophilic if a contact angle for a water droplet on the surface is less than 90 degrees (the contact angle is defined as the angle passing through the drop interior). Embodiments include hydrophilic surfaces with a contact angle from 90 to 0 degrees; Artisans will immediately appreciate that all ranges and values between the explicitly stated bounds are contemplated, with, e.g., any of the following being available as an upper or lower limit: 90, 80, 70, 60, 50, 40, 30, 20, 10, 5, 2, 0 degrees.

Materials for use in the process and/or biomaterials may include polymers. Hydrophilic polymers are useful, e.g., one or more polymers may be selected from polyvinyl alcohol (PVA), polyvinylpyrrolidone (PVP), polyethylene glycol (PEG), polyacrylic acid (PAA), polyacrylamide, hydroxypropyl methacrylamide, polyoxazolines, polyphosphates, polyphosphazenes, and polysaccharides, and variations of the same with an added iodine (e.g., PVA-I, PVP-I), or variations with further pendent groups, copolymers with one or more of PAA, PVA, PVP, or PEG, and combinations of the same. Two or more hydrophilic polymers may be intermixed together to form a nanoporous material. The molecular weight of the polymer can affect the properties of the biomaterial. A higher molecular weight tends to increase strength, decrease pore size, and decrease protein adsorption. Accordingly, embodiments include a polymer or a hydrophilic polymer having a molecular weight of 40 k to 5000 k daltons; Artisans will immediately appreciate that all ranges and values between the explicitly stated bounds are contemplated, with, e.g., any of the following being available as an upper or lower limit: 40 k, 50 k, 100 k, 125 k, 150 k, 250 k, 400 k, 500 k, 600 k 750 k, 800, 900 k, 1 million, 1.5 million, 2 million, 2.5 million, 3 million molecular weight.

The term PEG refers to all polyethylene oxides regardless of molecular weight or whether or not the polymers are terminated with a hydroxyl. Similarly, the terms PVA, PVP, and PAA are used without limitation as to terminal chemical moieties or MW ranges. References to polymers described herein include all forms of the polymers including linear polymers, branched polymers, underivitized polymers, and derivitized polymers. A branched polymer has a linear backbone and at least one branch and is thus a term that encompasses star, brush, comb, and combinations thereof. A derivitized polymer has a backbone that comprises the indicated repeating unit and one or more substitutions or pendant groups collectively referred to as derivitizing moieties. A substitution refers to a replacement of one atom with another. A pendant group is a chemical moiety attached to the polymer and may be the same or a different moiety as the polymer repeating unit. Accordingly, a reference to a polymer encompasses highly derivitized polymers and also polymers no more than 0.01-20% w/w derivitizing moieties, calculated as the total MW of such moieties compared to the total weight of the polymer. Artisans will immediately appreciate that all ranges and values between the explicitly stated bounds are contemplated, with, e.g., any of the following being available as an upper or lower limit: 0.01, 0.05, 0.1, 0.2, 0.3, 0.5, 1, 2, 3, 4, 5, 6, 7, 8, 9, 10, 15, 20% w/w.

A porous solid may be formed as a monolithic material, as a layer on another material, device, or surface, as a plurality of layers, or as one or more layers of a nanoporous material or a material that comprises a nanoporous material. Thus, for example, a plurality of layers may be extruded, with the layers being independently chosen to form one or more of: a nanoporous material, a microporous material, a hydrogel, a single-polymer material, a material having two or more polymers, and a non-nanoporous material.

The process of making the material can also affect the material properties, including the concentration of polymer in the polymeric mixture passed through a die. Starting PVA or other hydrophilic polymer concentrations may range from, e.g., 5 to 70% weight-volume (w/w) in water; generally about 10-30% (w/w) is preferable; Artisans will immediately appreciate that all ranges and values between the explicitly stated bounds are contemplated, with, e.g., any of the following being available as an upper or lower limit: 5, 10, 15, 20, 25, 30, 35, 40, 45, 50, 55, 60, 65, 70 percent.

Processes set forth herein may be truncated at a point before polymers crosslink and are processed to become a true nanoporous material, or otherwise adapted to avoid a nanoporous structure. In general, such materials have a lesser strength and toughness and lower solids content. Such materials are generally hydrogels when hydrophilic polymers are used at relatively low solids content. Accordingly, such materials, and even hydrogels, are contemplated herein, and materials may be made that are of somewhat lesser characteristics as compared to the nanoporous materials but, nonetheless, are superior to conventional processes and materials that use the same polymers. Similarly, and as a generalization, a microporous solid would have properties that approach those of the nanoporous materials and would have a strength better than those of a hydrogel.

Embodiments include a process for making a polymeric material comprising heating a mixture that comprises a water soluble polymer and a solvent to a temperature above the melting point of the polymer, extruding the mixture, and: cooling the mixture while removing the solvent and/or cooling the mixture while it crosslinks. When a plurality of polymers are present in a solvent, either with or without other additives, a melting point of the combined polymers in the solvent can be readily determined by the artisan, for instance by observing the mixture as it is heated and it passes from a cloudy to a markedly more translucent appearance. Further, after, or as part of, a formation process that uses the mixture, some or all of the solvent may be removed from the mixture while the cooling takes place. Embodiments include removing at least 50% w/w of the solvent in less than 60 minutes (or less than 1, 2, 5, or 10 minutes). Embodiments include removing at least 90% w/w (or at least 70% w/w or at least 80% w/w) of the solvent in less than 60 minutes (or less than 1, 2, 5, 10, or 30 minutes).

Products

Products, including end-user or intermediate products, or materials, may be made that have an aspect ratio as desired, e.g., at least 3:1, referring to materials set forth herein including nanoporous materials, microporous materials, and hydrogels. The aspect ratio increases as the device increases in length and decreases in width. Artisans will immediately appreciate that all ranges and values between the explicitly stated bounds are contemplated, with, e.g., any of the following being available as an upper or lower limit: 3:1, 4:1, 5:1, 6:1, 7:1, 8:1., 9:1, 10:1, 50:1, 100:1, 1000:1. A high aspect ratio is highly advantageous for certain devices, e.g., many types of catheters. In principle, a thin tube could be continuously extruded without limitation as to length. Such devices include, e.g., tubes, rods, cylinders, and cross-sections with square, polygonal, or round profiles. One or more lumens may be provided in any of the same. The devices may be made of a single material, essentially a single material, or with a plurality of materials including the various layers already discussed, or a reinforcing material, a fiber, a wire, a braided material, braided wire, braided plastic fibers.

The extrusion process, in particular, provides for concentric placement of a lumen; concentric is in contrast to eccentric meaning the lumen is off-center. In the case of a plurality of lumens, the lumens may be placed so that the lumens are symmetrically placed: the symmetry is in contrast to an eccentric placement of the lumens that is a result of a poorly controlled process. Embodiments include the aforementioned devices with an aspect ratio of at least 3:1 with lumens that are positioned without eccentricity or one lumen that is concentric with the longitudinal axis of the device.

The porous solids such as the nanoporous materials, microporous materials, and strong hydrogels may be used to make catheters or medical fibers. Examples of catheters are central venous, peripheral central, midline, peripheral, tunneled, dialysis access, urinary, neurological, peritoneal, intra-aortic balloon pump, diagnostic, interventional, drug delivery, etc.), shunts, wound drains (external including ventricular, ventriculoperitoneal, and lumboperitoneal), and infusion ports. The porous solids may be used to make implantable devices, including fully implantable and percutaneously implanted, either permanent or temporary. The porous solid materials may be used to make blood-contacting devices or devices that contact bodily fluids, including ex vivo and/or in vivo devices, and including blood contacting implants. Examples of such devices drug delivery devices (e.g., insulin pump), tubing, contraceptive devices, feminine hygiene, endoscopes, grafts (including small diameter<6 mm), pacemakers, implantable cardioverter-defibrillators, cardiac resynchronization devices, cardiovascular device leads, ventricular assist devices, catheters (including cochlear implants, endotracheal tubes, tracheostomy tubes, drug delivery ports and tubing, implantable sensors (intravascular, transdermal, intracranial), ventilator pumps, and ophthalmic devices including drug delivery systems. Catheters can comprise a tubular nanoporous material with a fastener to cooperate with other devices, e.g., luer fasteners or fittings. Radiopaque agents may be added to the materials, fibers, or devices. The term radiopaque agent refers to agents commonly used in the medical device industry to add radiopacity to materials, e.g., barium sulfate, bismuth, or tungsten.

Medical fibers made with porous solid materials include applications such as sutures, yarns, medical textiles, braids, mesh, knitted or woven mesh, nonwoven fabrics, and devices based on the same. The fibers are strong and pliable. Materials may be made with these fibers so that they are resistant to fatigue and abrasion.

Further Definition

The term medically acceptable refers to a material that is highly purified to be free of contaminants and is nontoxic. The term consists essentially of, as used in the context of a biomaterial or medical device, refers to a material or device that has no more than 3% w/w of other materials or components and said 3% does not make the device unsuited to intended medical uses.

Equilibrium water content (EWC) is a term that refers to the water content of a material when the wet weight of the hydrogel has become constant, and before the hydrogel degrades. In general, materials with a high solids content have been observed to be at equilibrium water content at 24-48 hours. A physiological saline refers to a phosphate buffered solution with a pH of 7-7.4 and a human physiological osmolarity at 37.degree. C. For purposes of measuring equilibrium water content, distilled water is used. The term w/v refers to weight per volume e.g., g/L or mg/mL. The terms biomaterial and biomedical material are used interchangeably herein and encompass biomedically acceptable materials directed to a use in the biomedical arts, for example, as implants, catheters, blood-contacting materials, tissue-contacting materials, diagnostic assays, medical kits, tissue sample processing, or other medical purposes. Moreover, while the materials are suited for biomedical uses, they are not limited to the same and may be created as general purpose materials.

The term molecular weight (MW) is measured in g/mol. The MW of a polymer refers to a weight average MW unless otherwise stated. When the polymer is part of a porous solid, the term MW refers to the polymer before it is crosslinked. When a distance between crosslinks is specified, it is the weight average MW between crosslinks unless otherwise indicated. The abbreviation k stands for thousand, M stands for million, and G stands for billion such that 50 k MW refers to 50,000 MW. Daltons is also a unit of MW and likewise refers to a weight average when used for a polymer.

Publications, journal articles, patents and patent applications referenced herein are hereby incorporated herein for all purposes, with the instant specification controlling in case of conflict. Features of embodiments set forth herein may be mixed and matched as guided by the need to make an operable process or product.

EXAMPLES

Example 1A

Extrusion of a PVA Porous Solid

The examples use the apparatus of FIG. 1 when an extrusion is described unless otherwise indicated. A 17% by weight PVA solution was prepared using 100 ml deionized water and 20 g PVA (85 kDa, Sigma-Aldrich). Water was heated to until water just began to boil (100.degree. C.) and then dry PVA was added slowly (over approximately 5-10 minutes) to the water while mixing moderately (mixer speed of approximately 40). Stopping the heating just as boiling begins to thereby prevent boiling is a process that is free of boiling. Once all PVA was added and solution began to thicken, heat was decreased to approximately 90.degree. C. and stir speed was increased to high so insure that the polymer completely dissolved and was fully blended. The PVA solution was stirred for approximately 2 hours. Upon completion, solution was thick and slightly opaque. Solution was poured into a 20 cc syringe and degassed in an oven at 90.degree. C.; heating/degassing does not typically exceed 2 hours.

The polymer sample was extruded into a bath of 13.degree. C. ethanol (Fisher, 190 proof) using a PTFE monofilament puller speed of 7 (ARDUINO specific motor moving software, 84 mm diameter puller wheel). Once the sample was extruded, it was left undisturbed in the cold ethanol for approximately 30 minutes before it was moved. The sample was then moved into a separate container of ethanol and placed in a freezer at −25.degree. C. for 24 hours. The monofilament was then removed from the sample by clamping the edge of the monofilament with tongs and slowly sliding the sample off. A mandrel slightly smaller than the inner diameter (0.033 in.) of the sample was inserted into the sample and the sample was dried flat in an incubator at 50.degree. C. for approximately 3 hours. After complete drying, samples were annealed by submerging in 120.degree. C. glycerol (Sigma-Aldrich) in a closed container for 24.+−.4 hours in oven. After annealing, samples were removed from glycerol and rinsed gently with deionized water. Samples were then transferred to a fresh container of deionized water to rehydrate for approximately 24 hours. Samples can be dehydrated and rehydrated without negative effects or changes to the porous solid being observed. This process produced a nanoporous solid material.

Example 1B

Molded PVA

PVA gels were prepared by weighing out 10 g of 85 k MW PVA (88% hydrolyzed) and adding to 100 mL of diH2O under agitation, heated to 80.degree. C. The PVA was added slowly and allowed to mix before elevating the temperature to 90.degree. C. The PVA solution was agitated until clarity was achieved. Approximately 5 mL of PVA solution was drawn into a syringe and degassed to remove entrapped air. The PVA solution was injected into a preheated mold at 60.degree. C., then rapidly cooled using a refrigerated cooling source. PVA gels were then removed intact on mandrels from the mold.

The PVA gels was quenched in a 6M solution of NaCl. The PVA gels were allowed to soak overnight in the salt solution (16-24 hrs), then removed. The hardened gels were then removed from the mandrels in their hydrated state to remove excess salt, and soaked for an additional 24 hrs in diH2O. Gels were then dehydrated to remove any residual water by drying for 24 hours at 25.degree. C.

Some of the gels were then annealed by submerging them in mineral oil and heating to 140.degree. C. for 1 hour. Gels were completely flushed and submerged in the oil to ensure no portion was exposed. Gels were allowed to cool, rinsed with 20 mL of diH2O, and then set to rehydrate in an additional 20 mL of diH2O at 37.degree. C. Other samples of the gels were annealed by submergence in glycerin and heating to 120-130.degree. C. for 3-24 hours. Gels were completely flushed and submerged in the glycerin to ensure no portion was left exposed to air. Gels were allowed to cool, rinsed with 20 mL of diH2O, and then set to rehydrate in an additional 20 mL of diH2O at 37.degree. C.

Example 2

Extrusion of PVA-Barium

A PVA-barium polymer solution was prepared using 100 ml of deionized water, 16 grams of barium sulfate (Sigma-Aldrich) and 4 g of 85 kDa PVA (Sigma-Aldrich). Water was heated until it just began to boil (100.degree. C.); dry barium sulfate was first added slowly and mixed until clumps are no long observed. Dry PVA was then added slowly (over approximately 5 minutes) to the water while mixing moderately. Once all PVA was added and solution began to thicken, heat was decreased to approximately 90.degree. C. and stir speed was increased to high so insure that the polymer completely dissolved and was fully blended. The PVA-barium solution was stirred vigorously for approximately 2 hours. Upon completion, solution was thick and white. Solution was poured into a 20 cc syringe and degassed in an oven at 90.degree. C.; heating during degassing does not typically exceed 2 hours.

Once the sample was extruded according to methods similar to those described in Example 1, it was left undisturbed in the cold ethanol for approximately 30 minutes before it was moved. The sample was then moved into a separate container of ethanol and placed in the freezer set at −25.degree. C. for 24 hours. The monofilament was then removed from the sample by clamping the edge of the monofilament with tongs, and slowly sliding the sample off. A mandrel slightly smaller than the inner diameter of the sample was inserted into the sample and the sample was dried flat in an incubator at 50.degree. C. for approximately 3 hours. After complete drying, samples were annealed by submerging in 120.degree. C. glycerol (Sigma-Aldrich) in a closed container for 24.+−.4 hours in oven.

After annealing, samples were removed from glycerol and rinsed gently with deionized water. Samples were then transferred to a fresh container of deionized water to rehydrate for approximately 24 hours. Samples can be dehydrated and rehydrated without negative effects or changes being observed.

Example 3

Rehydration/Dehydration Rates of PVA Porous Material

A percent loss of 55% was observed in PVA samples made as described in Example 1A as 3.5 French catheters over a 23 hour period. A plot of the weight loss over time in ambient air are show below in Table 2 and FIG. 9.

TABLE 2

| Weight loss over time of PVA sample in ambient conditions | |
|---|---|
| time (min) | weight (g) |
| 0.1 | 0.243 |
| 1 | 0.2026 |
| 2 | 0.2021 |
| 3 | 0.2015 |
| 4 | 0.2003 |
| 5 | 0.199 |
| 10 | 0.1931 |
| 15 | 0.1872 |
| 20 | 0.1824 |
| 25 | 0.1745 |
| 55 | 0.1533 |
| 80 | 0.1409 |
| 95 | 0.1345 |
| 100 | 0.1323 |
| 130 | 0.1256 |
| 135 | 0.1248 |
| 1405 | 0.1094 |

Example 4

Tensile Testing Example

Samples of PVA extrusions were made by heating a slurry of 17.6 g of bismuth subcarbonate and 100 g of 6.2 g/L of monosodium phosphate solution to 95 C jacketed reaction vessel and allowed to heat to temperature. To this, 25.8 g of PVA (Mowiol 28-99 or Sekisui Selvol 165, aka 67-99) was added over 5 min time period while mixing at 70% Run setting (D.I.T. CV2 Mixer). Polymer was mixed for 1 to 1.5 hours at 70% Run setting. Polymer was degassed at 90.degree. C. for less than 2 hours. Polymer then extruded into 5.degree. C. to 10.degree. C. in 190 proof ethanol and stored at ambient conditions for at least 30 minutes.

The polymer was dried for 3 hours at 55.degree. C. and annealed for 1.5 hours at 140.degree. C. in a forced convection oven. The samples were then rehydrated for 2 hours in 1.times.PBS in 37.degree. C.

Figure 10:
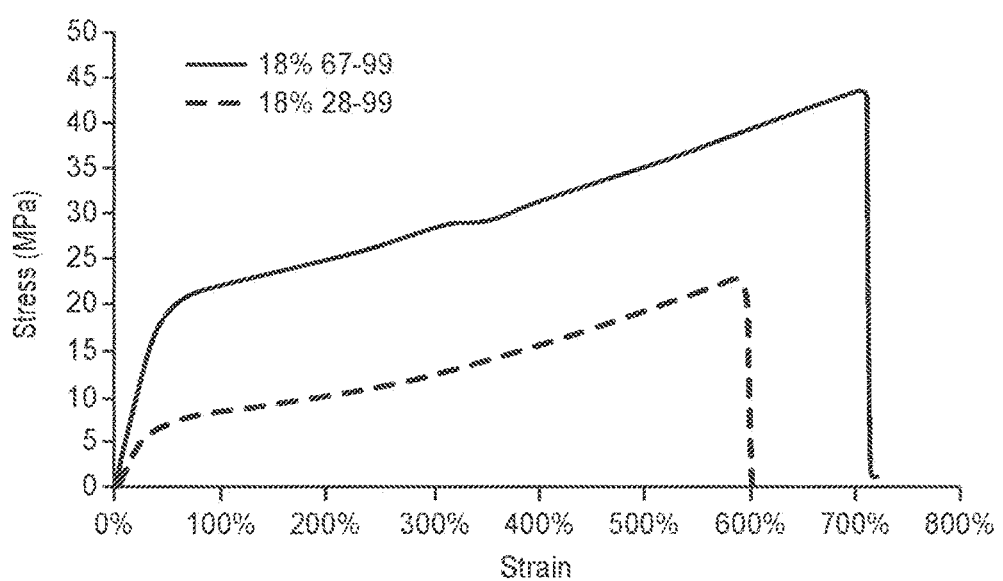
FIG. 10 is a plot of tensile test data for a porous solid made according to Example 4, with the higher molecular weight polymer (PVA 67-99) providing a greater modulus and tensile strength than the lower molecular weight polymer (PVA 28-99)

Tensile strength (Stress) was measured in Newtons on a Mark 10 Tensile Tester (Model DC4060) with a 100N digital force gauge (Model #M5-1006). Using calipers (Mark 10 Model #500-474) to measure the outer diameter and a pin gauge set to measure inner diameter, a cross sectional area was determined for the samples. PVA 67-99 indicates nominal viscosity (as a 4% solution in water) of 67 cPs with greater than 99% hydrolysis. PVA 28-99 indicates nominal viscosity (as a 4% solution in water) of 28 cPs with greater than 99% hydrolysis. The viscosity of the PVA is positively correlated to the molecular weight of the polymer. Table 3 and FIG. 10 show an increase of Young's Modulus as well as maximum tensile stress with an increase of PVA viscosity.

TABLE 3

| Stress-Strain characteristics of PVA 28-99 vs PVA 67-99 | | |
|---|---|---|
|  | PVA 28-99 | PVA 67-99 |
| Bismuth Subcarbonate (w/w % solids) | 40% | 40% |
| % w/w PVA in Batch | 18% | 18% |
| Outer Diameter (mm) | 1.55 |  |
| Inner Diameter (mm) | 0.69 | 0.76 |
| Cross Sectional Area (mm$^2$) | 1.52 | 1.22 |
| Max Stress (N/mm$^2$) | 22.7 | 43.4 |
| Modulus (MPa) | 20.6 | 49.1 |
| Maximum Elongation | 595% | 705% |

Samples of 18% PVA extrusions were made by heating a slurry of 17.6 g of bismuth subcarbonate and 100 g of 6.2 g/L of monosodium phosphate solution to 95.degree. C. jacketed reaction vessel and allowed to heat to temperature. To this, 25.8 g of PVA (MOWIOL 28-99) was added over 5 min time period while mixing at 70% Run setting (D.I.T. CV2 Mixer).

Samples of 22% PVA extrusions were made by heating a slurry of 23.3 g of bismuth subcarbonate and 100 g of 6.2 g/L of monosodium phosphate solution to 95.degree. C. jacketed reaction vessel and allowed to heat to temperature. To this, 35.0 g of PVA (MOWIOL 28-99) was added over 5 min time period while mixing at 70% Run setting (D.I.T. CV2 Mixer).

Samples of 26% PVA extrusions were made by heating a slurry of 35.4 g of bismuth subcarbonate and 115.9 g of 6.2 g/L of monosodium phosphate solution to 95.degree. C. jacketed reaction vessel and allowed to heat to temperature. To this, 53.2 g of PVA (MOWIOL 28-99) was added over 5 min time period while mixing at 70% Run setting (D.I.T. CV2 Mixer).

Each set of polymer was mixed for 1.5 to 2 hours at 70% Run setting. Polymer was degassed at 90.degree. C. for less than 2 hours. Polymer then extruded into 5.degree. C. to 10.degree. C. in 190 proof ethanol and store at ambient conditions for at least 30 minutes.

The polymer was dried for 24 hours in a vacuum oven at 40.degree. C. and annealed for 1 hour in silicone oil at 140. The samples were rinsed with 190 proof ethanol 3 times then rehydrated for 2 hours in 1.times.PBS in 37.degree. C. Various preparations are described in Table 4.

TABLE 4

First preparation

|  | 18% PVA 28-99 | 22% PVA 28-99 | 26% PVA 28-99 |
|---|---|---|---|
| % w/w PVA in Batch | 18.0% | 22.0% | 26.0% |
| Bismuth Subcarbonate | 12.0% | 14.7% | 17.3% |
| 3.2 g/L Monosodium Phosphate Solution | 70.0% | 63.3% | 56.7% |

Figure 11:
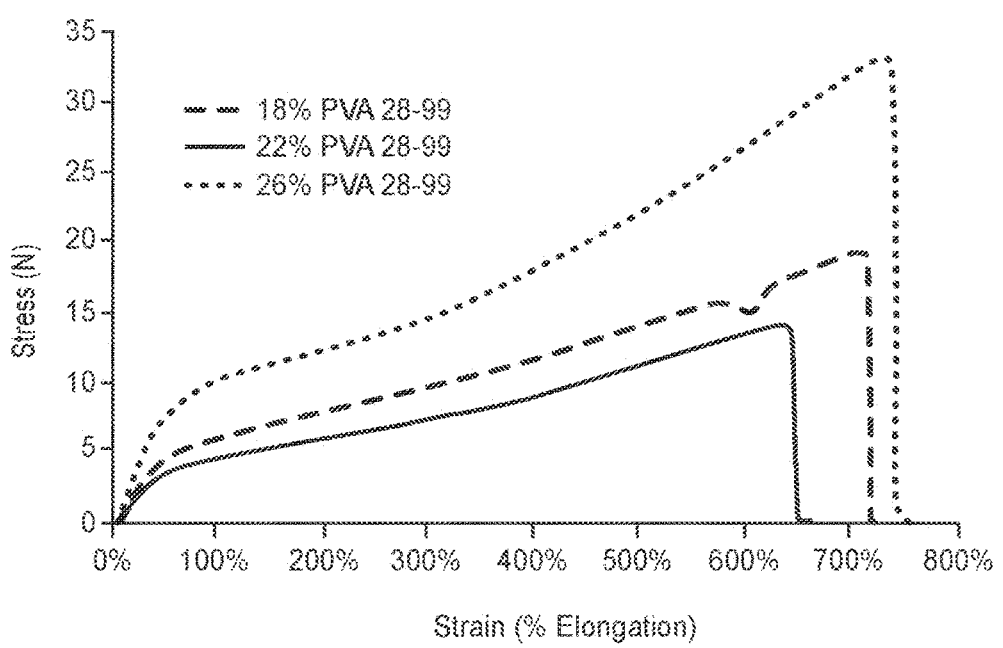
FIG. 11 is a plot of tensile test data for a porous solid made according to Example 4, with the highest concentration of the polymer (26%) providing the material of greatest modulus and tensile strength relative to lower polymer concentrations (22% or 18%)

PVA in the mixtures of Table 4 was increased a hatching step in relation to monobasic salt solution. An increase in PVA provided a higher maximum tensile strength and a higher Young's Modulus. With an increase in a ratio of PVA to monosodium phosphate, a stronger material can be prepared. FIG. 11 and Table 5 show that 26% PVA 28-99 has an increase in Young's Modulus and Maximum Tensile Stress compared to 22% and 18% PVA 28-99.

TABLE 5

Increase of PVA in the batch

|  | 18% PVA 28-99 | 22% PVA 28-99 | 26% PVA 28-99 |
|---|---|---|---|
| Bismuth Subcarbonate (wt % solids) | 40% | 40% | 40% |
| % PVA in Batch | 18% | 22% | 26% |
| Outer Diameter (mm) | 1.32 | 1.40 | 1.48 |
| Inner Diameter (mm) | 0.71 | 0.71 | 0.76 |
| Cross Sectional Area (mm$^2$) | 0.97 | 1.14 | 1.26 |
| Max Stress (N/mm$^2$) | 19.3 | 14.1 | 33.2 |
| Modulus (MPa) | 14.0 | 10.8 | 18.5 |
| Maximum Elongation | 729% | 665% | 755% |

Example 5

Attachment of Extension Tube/Luer Lock to Hydrogel

A luer lock was bonded via cyanoacrylate to a polyurethane (PU) extension tube. The extension tube was mated to the PVA catheter body by sliding over PVA catheter body approximately 0.5 in. A heat gun used at approximately 300.degree. F., PU/PVA overlap exposed 10.times. at 0.5 s intervals, process repeated until infusion bonding of PU and PVA occurred. Tensile data was evaluated for multiple samples:

TABLE 6

Tensile data for luer lock attached to PVA porous material

| Sample# | Tensile Strength (lbs) | OD(in) |
|---|---|---|
| 1 | 3.130 | 0.070 |
| 2 | 5.600 | 0.082 |
| 3 | 6.090 | 0.095 |
| 4 | 6.810 | 0.095 |
| 5 | 3.940 | 0.094 |
| 6 | 3.440 | 0.094 |
| 7 | 2.830 | 0.080 |
| 8 | 4.360 | 0.079 |
| 9 | 1.800 | 0.043 |
| 10 | 3.220 | 0.049 |
| 11 | 4.660 | 0.060 |

Further testing showed that a conventional ethylene-vinyl acetate (EVA) bonding process for attaching extensions or other devices to a catheter was effective for bonding such devices to an extruded porous PVA material. Table 7 shows results wherein the points of attachment exceeded the PVA strength or otherwise exceeded all design requirements. A standard natural color EVA melt-liner 3/16 in. O.D. with 0.014 in. wall and Polyolefin RNF 0.25 in. heatshrink were used in conjunction with PVA tubes (0.050 in. ID/0.063 in.-0.065 in. OD) and luer hub with tube assemblies (0.062 in. ID/0.101 in. O.D.) A Steinel HG2310 LCD heat gun with temperature set at 400.degree. F.; (nozzle is 0.25 in. dia. size and modified tip to be 0.12 in. wide by compression to provide a narrow heat zone area) and 0.050 in. stainless mandrels inserted through the luer hub/tube assemblies into the ID of the PVA tubes.

Three samples using a PE hub and PVA tube butt weld were made at 400.degree. F. The joint was observed to be very strong.

The clear luer hub and tube assembly was slipped over the PVA extrusion about 0.75 in. deep and the ethyl vinyl acetate melt liner and polyolefin added over the assembly. A melt was made and joined at 400.degree. F. Upon noticing the melting of the PVA extrusion and meltliner, a more controlled shrinking method was employed using gentle hand-rolling of the melted joint to shape smooth and prevent melting of the PVA tube.

The PVA extrusion was inserted inside the hub and tube and joined using the methods described above. The strength was very good. Assemblies could not be pulled apart by hand. Two samples were formed and used for hydration and testing. Samples were tensile tested after two hours of conditioning in PBS at 37.degree. C., with results shown in Table 7.

TABLE 7

| Sample | Tensile (N) | Failure Mode/Point | Travel Distance (mm) |
|---|---|---|---|
| PE Extension Tube 1 | 12.07 | Catheter tube | 28.27 |
| PE Extension Tube 2 | 11.74 | In EVA bond | 40.78 |
| PU Extension Tube 1 | 10.53 | Catheter tube | 30.28 |
| PU Extension Tube 2 | 9.69 | Catheter tube | 91.38 |
| PU Extension Tube 3 | 9.28 | Catheter tube | 85.96 |

Attachment of a suture wing d was also successful. An injection-mold of a suture wing was made with EVA (Ateva 2803G with 20% bismuth subcarbonate). It conjoined an extension line (HTP Meds #2006-0335 Rev A) and a PVA tube. A maximum break force of 27 N (6.1 lbf) (Wagner Instruments #FDK 30) required to disconnect the PVA tube and the EVA suture wing. When the assembled PICC was hydrated the break force was 28 N (6.2 lbf).

Example 6

Radiopacity

Samples were made according to methods of Example 2. The samples are depicted in FIGS. 12A-12F: Control (12A, BARD PowerPICC), 5.7% bismuth subcarbonate by weight, not annealed (21B), 12.1% bismuth subcarbonate by weight, not annealed (12C), 12.1% bismuth subcarbonate by weight, annealed (12D), 5.7% bismuth subcarbonate by weight, annealed (12E), 4.2% bismuth subcarbonate by weight (12F).

All samples B-E exceed radiopacity of control sample. 4.2% bismuth subcarbonate sample (12F) showed about the same level or less of radiopacity and is considered a minimum for the samples. Radiopacity testing was performed at Mount Auburn Hospital in Cambridge, Mass.

Example 7

Power Infusion

Pressure testing showed that the extruded porous plastics exceeded all design requirements. Power injection testing was performed for samples of PVA-RO (radioopaque) agent incorporated nanoporous solid made according to Example 2 using a Medrad MARK V PLUS POWER INJECTOR. Samples were attached to a barbfluer fitting with silicone tubing.

Water was injected at 5 mL/sec for 1 second with the sample not occluded (free flowing) and passed without sample failure. Another same sample for the same PVA-RO formulation was then occluded and tested using the same parameters; the sample failed at the extension tube bond due to preexisting damage caused by heat shrink processing.

Figure 13:
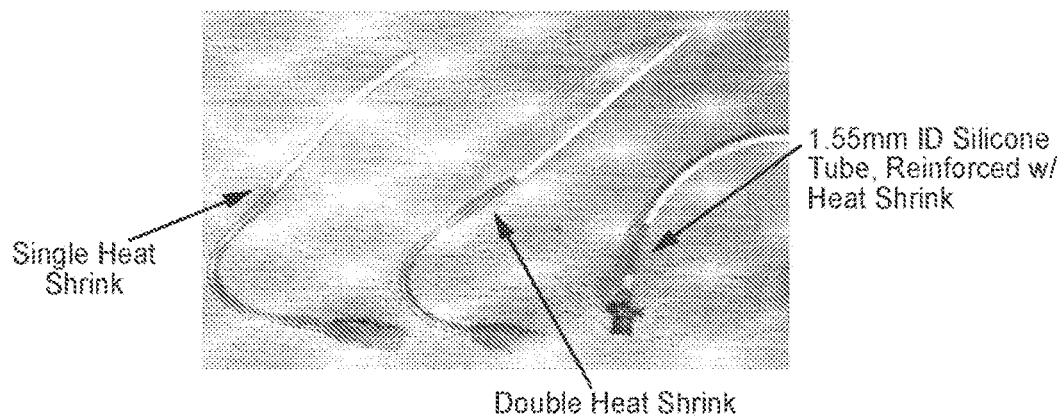
FIG. 13 is a photograph of a first set of test samples described in Example 7.
Figure 14:
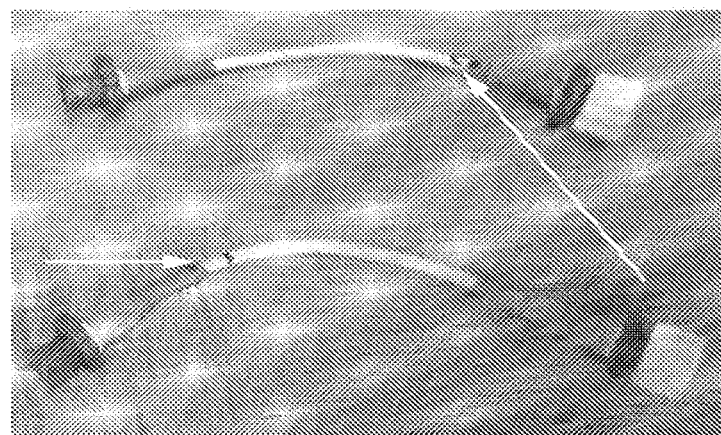
FIG. 14 is a photograph of a second set of test samples described in Example 7.

Another set of samples shown in FIG. 13 were then attached to barbed fittings with Loctite 4902 on silicone tubing and heatshrink using methods described in Example 5; a barb was attached to each end of the sample to allow capping for occlusion testing. Samples 1 and 2 were testing using a flow rate of 5 mL/sec, with a total liquid volume of 5 ML at 100 PSI; samples failed near heat shrink joints due to bonding heat exposure (failure locations indicated in FIG. 14).

Sample 3 was tested using a reduced injection rate and volume and passed 2 of 3 cycles for the following cycles: Cycle 1 used a flow of 0.4 mL/sec and 1 mL total volume at 100 max PSI, cycle 2 used the same parameters with 200 max PSI; both cycles passed. Cycle 3 used a flow of 5.0 mL/sec with 1 mL total volume and 350 max PSI; failure occurred with the tube separated from silicone and heatshrink; no damage to hydrogel was observed, indicating that using the proper attachment method (i.e., overmolding), the PVA extruded tubes were capable of withstanding power injection.

Example 8

Contact Angle

Contact angle was determined for PVA-RO incorporated hydrogel made according to Example 2. A 1 cm section of extruded material was cut from main strand using an exacto knife; sample was then carefully cut along length of section. Loctite 406 used to carefully attach sample to a glass slide; once fully adhered, Locate 406 was dabbed along edged of sample and walls of samples were gently pushed onto glass slide with forceps until a flat configuration was achieved. Using a 20 .mu.l pipettor, a single small drop of colored water was dropped onto the surface of the material; drop was immediately photographed and imported to an image viewer to measure contact angle of droplet. All surfaces and camera were leveled prior to testing. The sample had a contact angle of 60.degree. (taken through the drop) as measured by the drop test.

Example 9

SEM Results

Figure 15A:
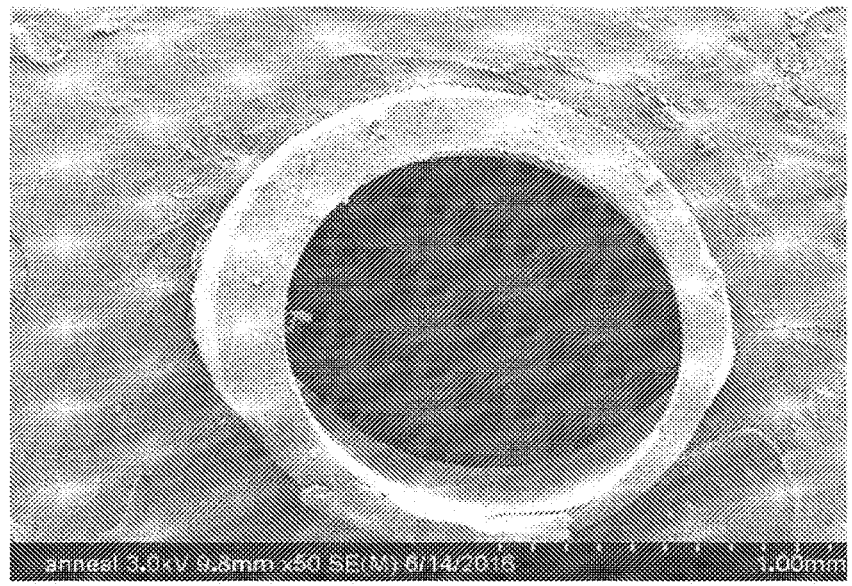
FIGS. 15A-15B are scanning electron micrographs (SEM) of transverse (15A) or longitudinal (15B) cross sections of a porous solid extruded as described in Example 8.
Figure 15B:
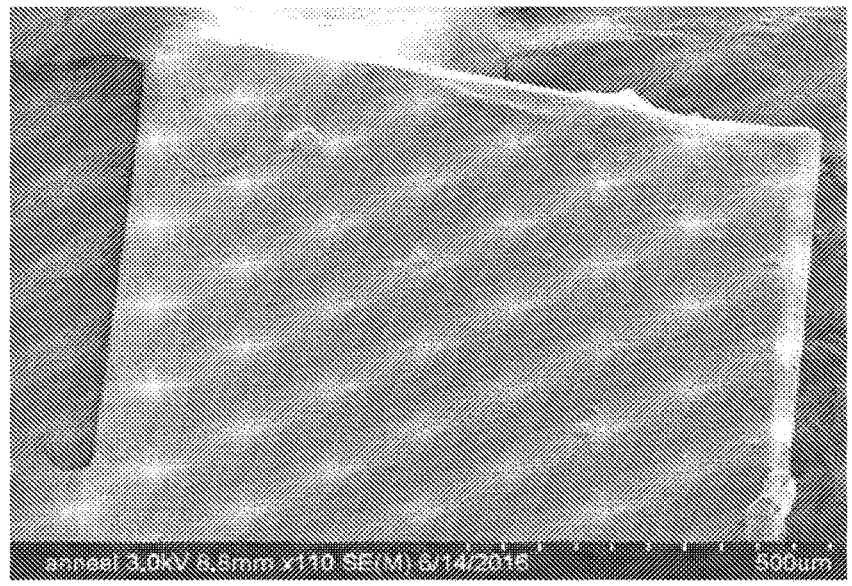

FIGS. 15A-15B are SEM images of a 17% PVA solution extruded using the methods of Example 1A except as otherwise specified. Samples were hydrated in distilled water for 24 hours at 37.degree. C. and then rapidly frozen using liquid nitrogen to preserve pore structure. Samples were then lyophilized for 48 hours to remove water, and submitted for SEM analysis. FIG. 15A shows a cross section of an extruded PVA tube, showing no macroporosity in the gel structure. FIG. 15B shows a longitudinal cross section of the extruded tube at a higher magnification, demonstrating no macroporosity to the structure. This material had a high water content and is highly porous, with the pores no more than about 10 nm in diameter.

Figure 16A:
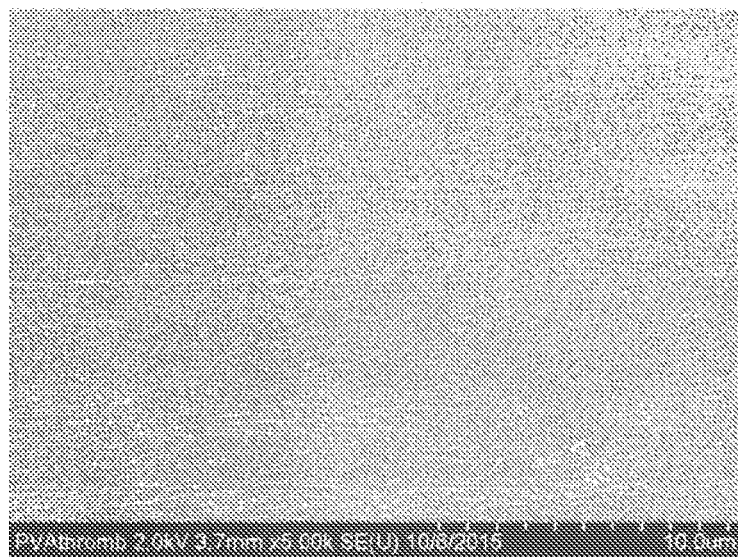
FIGS. 16A-16D are SEMs of a hydrophilic nanoporous material prepared as described in Example 9, provided at various magnifications as indicated by the scale bars.
Figure 16B:
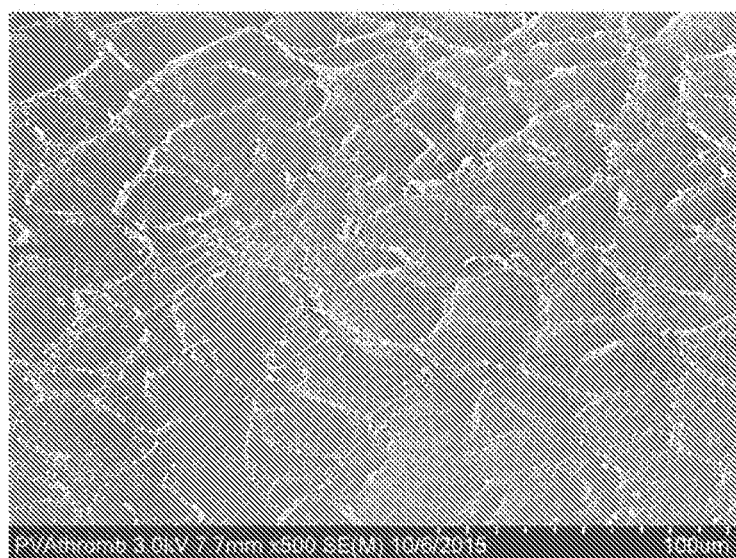
Figure 16C:
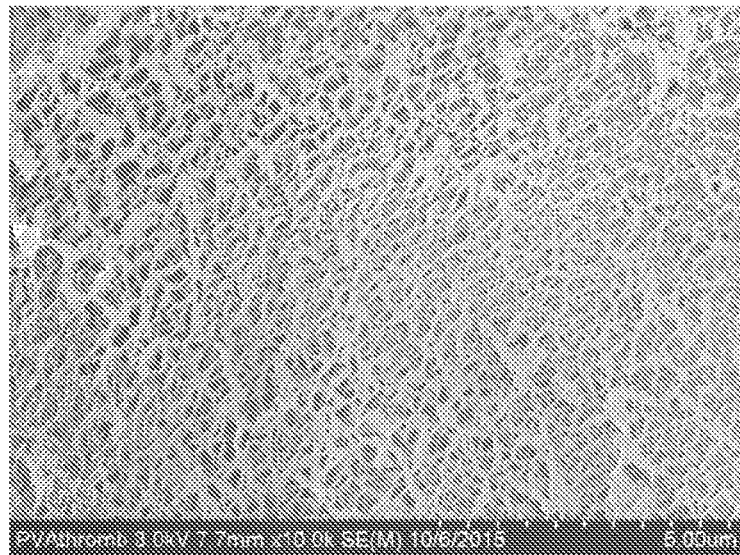
Figure 16D:
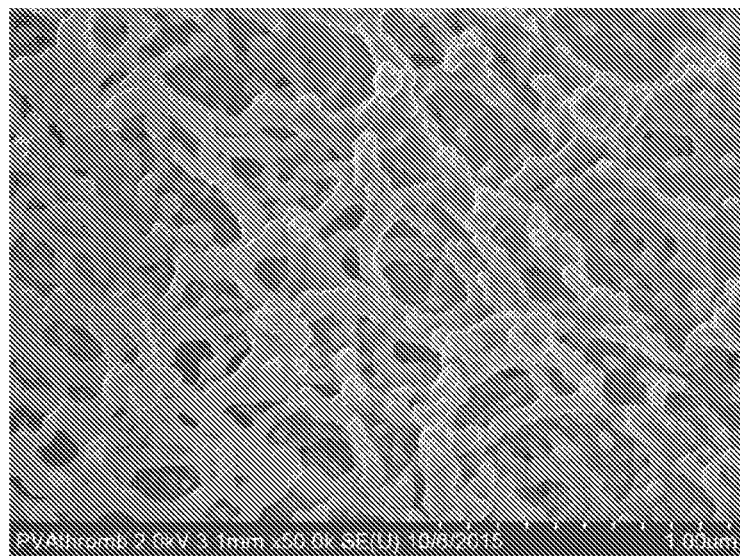

Samples of PVA extrusions were also made by heating 200 g distilled water to 95.degree. C. jacketed reaction vessel and allowed to heat to temperature. To this, 40 g of PVA (Sigma, 146 k-186 k) was added over 5 min time period while mixing at 200 RPM. Polymer was mixed for 1.5 hours at 300 RPM. Polymer was degassed at 90.degree. C. for less than 2 hours. Polymer then extruded into -23.degree. C. ethanol with the apparatus of FIGS. 1-3 and then stored in ethanol at -25.degree. C. in freezer for 24 hours. Samples were dried for 6 hours. After drying, samples were submerged in 120.degree. C. glycerol for 17 hours. After annealing, samples removed and allowed to cool before being rinsed with ethanol cores removed after rinse. Samples dried for 12 hours at 50.degree. C. Two SEM images, FIGS. 16A-16D, show the results. FIGS. 16C-16D are taken at a high magnification demonstrating nanoporosity.

Example 10

Salt Additives

Various salts were used in the hatching process, referring to the process of driving the polymer into solution in the polymer-solvent mixture, to alter the maximum tensile stress and Young's Modulus. Multifunctional salts were used such as phosphoric acid, boric acid, and citric acid. These salts were added in at varying degrees of neutralization as sodium and/or potassium salts.

PBS (phosphate buffered saline) contains sodium chloride, potassium chloride and phosphate salts as it major constituents. Three neutralization points where analyzed in comparison to PBS. A mixture of 18% PVA (MW 146 k-186 k, Sigma Aldrich #363065), 6% bismuth subcarbonate (Foster) (20 wt % based on solids) and a constant molar ratio of these phosphate salt solutions at 51.7 nM was examined with phosphoric acid (Sigma Aldrich), monosodium (Sigma Aldrich), and disodium phosphate (Sigma Aldrich) in water. Monosodium phosphate resulted in the highest Young's Modulus, where phosphoric acid produced the highest tensile. FIG. 17A is a plot of tensile strengths for 18% PVA samples compounded with PBS, monosodium phosphate, disodium phosphate and phosphoric acid. The effect of other multifunctional (two or more neutralization sites) salts were also evaluated, with results as plotted in FIG. 17B. Boric acid (Sigma Aldrich), citric acid (Sigma Aldrich) and phosphoric acid (Sigma Aldrich) are compared at 18% PVA (Sigma Aldrich), 6% bismuth subcarbonate (Foster) (20 wt % based on solids) with 51.7 mM of the respective acid solution Boric acid increased both Young's Modulus and maximum tensile stress, whereas citric acid and phosphoric acid are relatively the same.

Example 11

PVA and PAA Blend Batching and Copolymer Extrusion

PVA-PAA blend solutions were batched using the following method; see Table 8 for formulation composition. 100 g water and PVA were added to high viscosity jacketed vessel heated to 90.degree. C. and mixed at 600 RPM. Bismuth subcarbonate concentrate was homogenized with remaining water for 15 minutes and then 32 g of the concentrate was added to 90.degree. C. jacketed reaction vessel, unless otherwise specified. PVA was then added to vessel while mixing 600 RPM. PAA was added to solution after 1 hour of mixing and continued for 0.5 hours until solution was totally homogenous. Polymer was then aliquoted into 20 mL syringes.

TABLE 8

PVA-PAA Blend Formulation Composition

| No. | % PAA | Molecular Weight PAA | g PVA | g Water | g Bismuth Subcarbonate Concentrate | g PAA |
|---|---|---|---|---|---|---|
| 1 | 0.1 | 450 k | 16.0 | 100 | 32.0 | 0.125 |
| 2 | 0.4 | 450 k | 16.0 | 100 | 32.0 | 0.500 |
| 3 | 4.0 | 450 k | 16.0 | 100 | 7.0 (RO only) | 5.125 |
| 4 | 0.2 | 3 m | 16.0 | 100 | 10.0 (RO only) | 0.500 |
| 5 | 0.3 | 3 m | 16.0 | 100 | 32.0 | 0.500 |
| 6 | 0.4 | 3 m | 16.0 | 100 | 7.0 (RO only) | 0.500 |

Polymer was reheated to 90.degree. C., and degassed at 90.degree. C. for 1 hour. Polymer was then extruded into approximately 10.degree. C. to approximately 21.degree. C. ethanol. Extrudate was allowed to sit in ethanol on monofilament for approximately 0.5 hours. Extrudate was then transferred to room temperature ethanol and allowed to dehydrate for 24 hours with monofilament removed.

Extrudate was transferred to vacuum oven and dried at 50.degree. C. for 48 hours. After drying, samples were injected with 120.degree. C. USP grade mineral oil and then submerged in 120.degree. C. mineral oil in a convection oven for 2 hours. Samples were then removed from mineral and allowed to cool to room temperature. A rinse/flush procedure was performed once with ethanol and twice with distilled water. Samples transferred to 37.degree. C. PBS to hydrate before tensile testing and surface evaluation. Tensile testing was performed as per ISO-10555 protocols Tensile values are not normalized to sample cross sectional area.

Figure 18B:
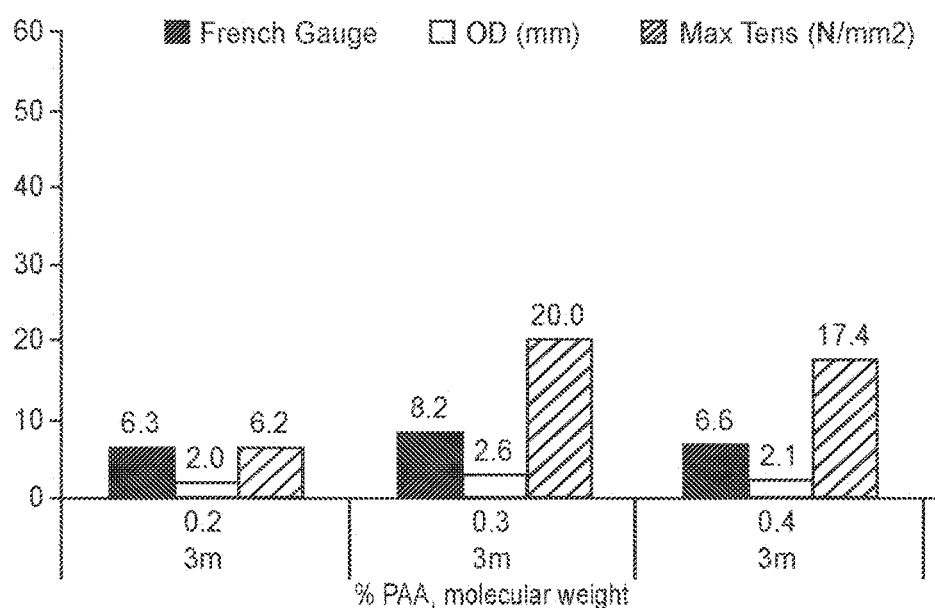

FIG. 18A is a comparison of PVA-PAA blend formulations of 450 k molecular weight PAA. PAA formulations at 0.1% and 0.4% (w/w) concentrations in water extruded with PVA in an 11-13% concentrations showed higher tensile strength than 4.0% formulations. Higher water content may be correlated to increased percent of PAA, decreasing of strength between PVA bonds, therefore reducing tensile strength. Moreover, the 4.0% 450 k PAA formulations exhibited a spongey looking surface. FIG. 18B is a comparison of PVA-PAA Blend Formulations of 3-m Molecular Weight PAA. PAA formulations of 3-m molecular weight at 0.3% and 0.4% (w/w relative to solvent) concentration showed higher tensile strength than 0.2% formulation. The 3 m molecular weight PAA-containing formulations exhibited approximately half of the tensile strength of 450 k PAA-containing formulations, excluding 4.0%.

Example 12

PVA and PEG Blend Batching and Copolymer Extrusion

PVA-PEG blend solutions were batched using the following method; see Table 9. PVA (Sigma, 146 k-186 k), bismuth subcarbonate (Foster), 100 g distilled water, and PEG 8 k (Sigma), PEG 20 k (Sigma,), or PEG 35 k (Sigma). Bismuth subcarbonate was homogenized with water for 15 minutes and then added to 90.degree. C. jacketed reaction vessel. PVA was then added to vessel while mixing at 600 RPM for 2 hours; PEG was then added to solution and mixing continued for 2 hours until solution was totally homogenous. Polymer was then aliquoted into 20 mL syringes.

TABLE 9

PVA-PEG Blend Formulation Composition

| No. | % PEG | Molecular Weight PEG | gPVA | g Water | g Bismuth Subcarbonate | gPEG |
|---|---|---|---|---|---|---|
| 1 | 1 | 8 k | 16.0 | 100 | 7.0 | 1.25 |
| 2 | 1 | 20 k | 16.0 | 100 | 7.0 | 1.25 |
| 3 | 1 | 35 k | 16.0 | 100 | 7.0 | 1.25 |

Polymer was reheated to 90.degree. C. and extruded into approximately 3.degree. C. to 21.degree. C. ethanol. Extrudate was allowed to sit in ethanol on monofilament for approximately 1 hour. Extrudate was then transferred to room temperature ethanol and allowed to dehydrate for 24 hours with monofilament removed.

Figure 19:
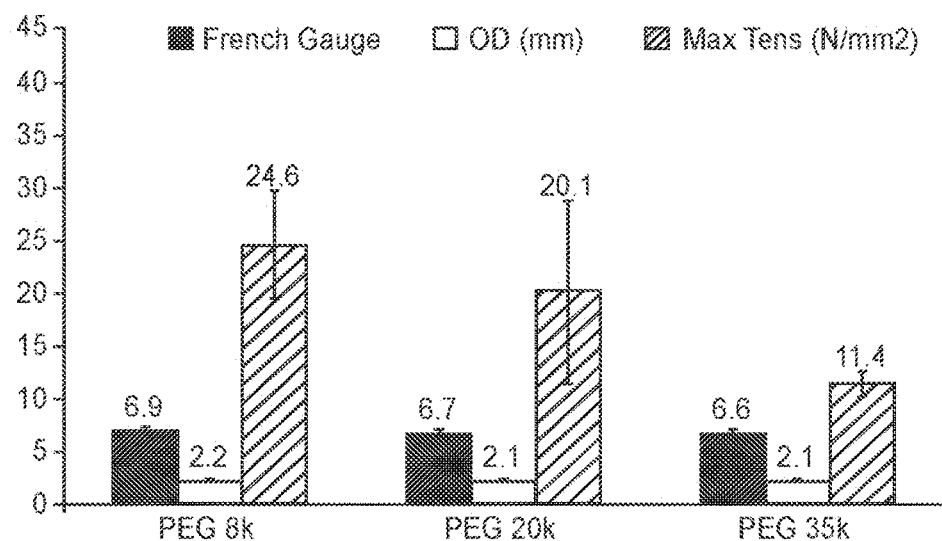
FIG. 19 is a plot of tensile data for various blends of polymers described in Example 12, with data being shown in N/mm·sup.2.
Figure 20A:
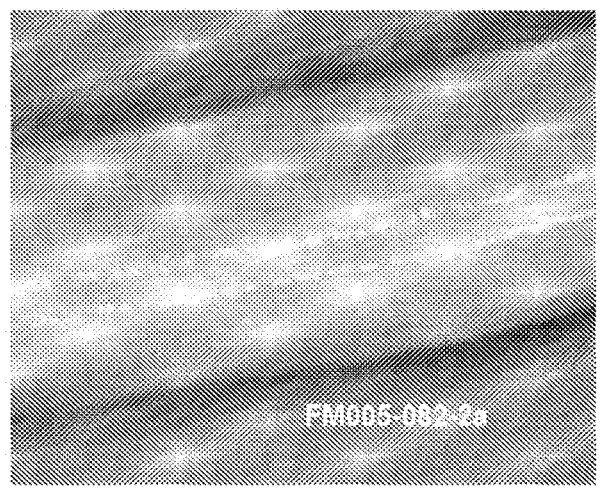
FIGS. 20A-20C are photograph of a PEG/PVA copolymer extrusion described in Example 12 depicting surfaces with a PEG molecular weight of 8 k (20A), 20 k (20B), or 35K (20C)
Figure 20B:
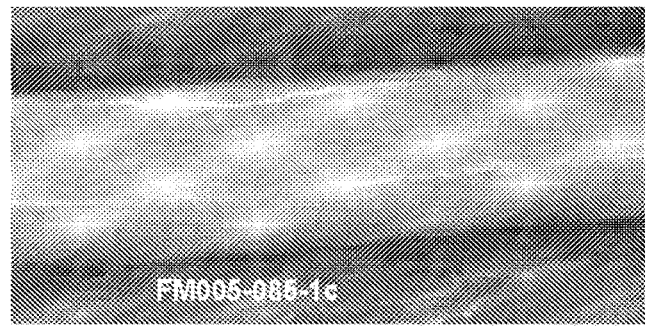
Figure 20C:
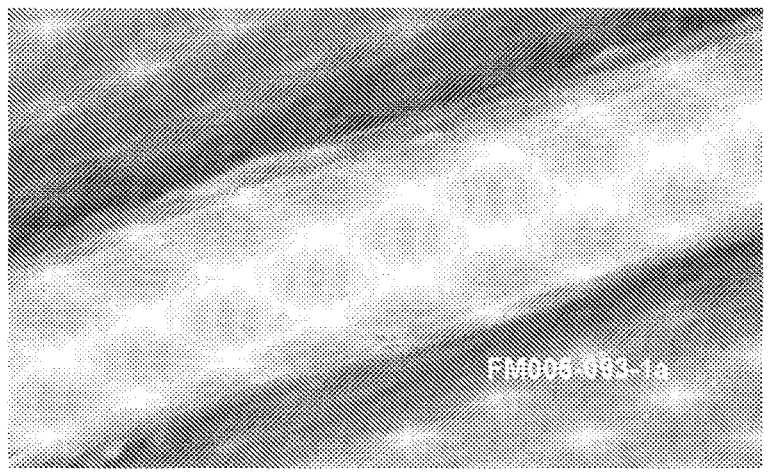
Figure 21A:
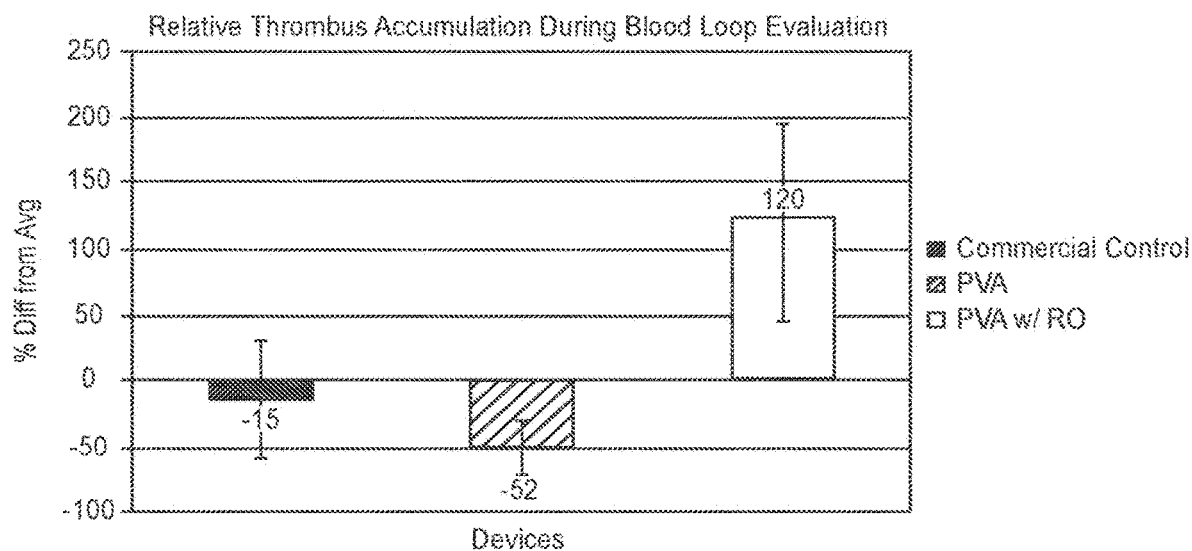
FIGS. 21A-21B provide results of blood contact experiments described in Example 15 as a plot of relative thrombus accumulation (21A) or photographs of the tested samples (21B).

Extrudate was transferred to vacuum oven and dried at 50 C for 48 hours. After drying, samples were injected with 120.degree. C. USP grade mineral oil and then submerged in 120.degree. C. mineral oil in a convection oven for 2 hours. Samples were then removed from mineral and allowed to cool to room temperature. A rinse/flush procedure was performed once with ethanol and twice with distilled water. Samples transferred to distilled water to hydrate before tensile testing and surface evaluation. Tensile testing was performed as per ISO-10555 protocols. FIG. 19 depicts the results and shows a comparison of PVA-1% PEG formulations of varying MW PEG; note that tensile values are not normalized to sample cross sectional area. PEG blend extrudate resulted in a smooth surface, excluding PEG 35 k which produced a scale pattern along outside of extrudate. Due to wide standard deviations of all 1% PEG blends, there is no significant difference observed in tensile strength of 8 k, 20 k 35 k PEG co-extrusions. FIGS. 20A-20C are photographs of the 8 k, 20 k, 35 k, PEG co-extrusions, respectively.

Example 13

Thrombogenic Evaluation of a PVA Gel

Samples of PVA extrusions were made by heating 200 g distilled water to 95.degree. C. jacketed reaction vessel and allowed to heat to temperature. To this, 40 g of PVA (Sigma, 146 k-186 k) was added over 5 min time period while mixing at 200 RPM. Polymer was mixed for 1.5 hours at 300 RPM. Polymer was degassed at 90.degree. C. for less than 2 hours. Polymer then extruded into −23.degree. C. ethanol and then stored in ethanol at −25.degree. C. in freezer for 24 hours. Samples were dried for 6 hours. After drying, samples were submerged in 120.degree. C. glycerol for 17 hours. After annealing, samples removed and allowed to cool before being rinsed with ethanol; cores removed after rinse. Samples dried for 12 hours at 50.degree. C.

Samples of PVA with barium sulfate were made by heating 50 g water in a jacketed reaction vessel at 90.degree. C. In a side vessel, 4 g of barium sulfate and 50 g water homogenized for 15 minutes at ilk RPM and then added to the jacketed vessel. This was mixed for 10 minutes to heat.

After heating, 16 g of PVA (Sigma, 146 k-186 k) was added and mixed at 360 RPM for approximately 2 hours.

The PVA-RO polymer mixture was heated to 90.degree. C. and extruded into −16.degree. C. ethanol. The extrudate was allowed to dehydrate at −25.degree. C. for 24 hours. Cores were removed and samples dried in an incubator at 50.degree. C. for approximately 6 hours. After drying, samples were submerged in 120.degree. C. glycerol (Sigma) for 17 hours. After annealing, samples removed and allowed to cool before being rinsed with distilled water. Samples dried at 50.degree. C. for 12 hours and packaged for testing.

Samples were evaluated for antithrombotic durability testing at Thrombodyne, Inc. (Salt Lake City, Utah). Each sample was cut to 15 cm in length with an N=5 per sample group. Prior to testing, samples were sterilized using a 12 hour ethylene oxide exposure; samples were hydrated for approximately 48 hours in distilled water prior to evaluation to represent clinical use.

Fresh heparinized bovine blood with autologous 111In-labeled platelets was divided into portions for test sample and control evaluation. Samples were inserted into an in vitro blood flow loop of 0.25 in. ID polyvinyl chloride tubing for approximately 120 minutes. Blood was kept at 98.degree. C. and pumped through the blood loop using a peristaltic pump for the duration of testing. Samples were initially checked for thrombi after 45 minutes in the blood flow loop, and removed at 120 minutes. At the end of the experiment, the devices were explanted from the tubing, rinsed with saline, and placed in a gamma counter for thrombus quantification. Experiment parameter are presented in Table 10. Each experiment consisted of an independent flow system per test sample and/or control circulating blood from the same animal to enable simultaneous comparisons without cross-over effects.

Figure 21B:
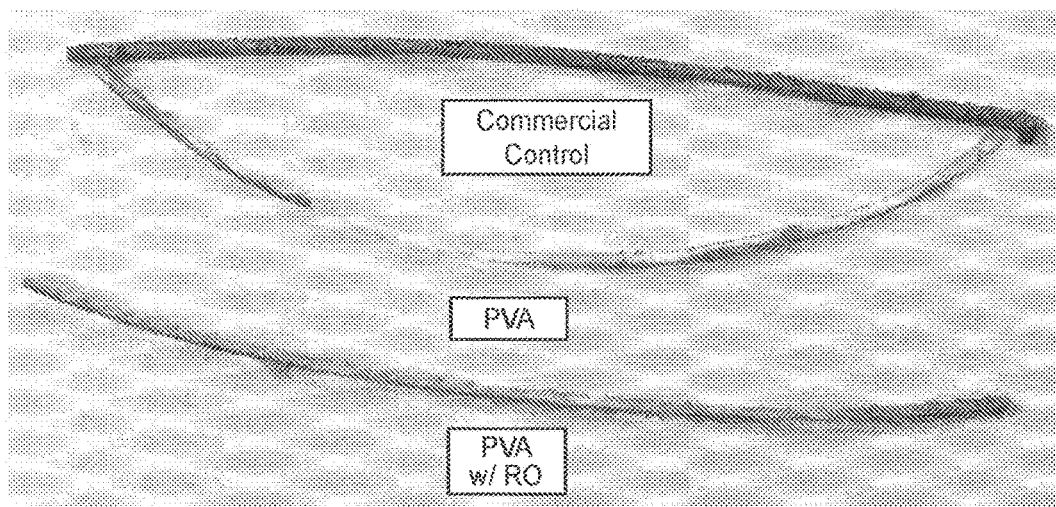

Samples were measured for radioactivity and also qualitatively assessed for specific types of thrombus accumulation (i.e. adhesion or fibrin accumulation). Count results are provided in Table 10. Percent thrombosis was calculated relative to the average total thrombosis observed across all test and control groups per animal blood circulated. Results for thrombus accumulation are provided in Tables 11-12 and depicted in FIG. 21A. Visual assessment of the thrombosis is shown in FIG. 21B, with a commercially available control catheter, a 17% PVA extrusion, and the 17% PVA-barium sulfate extrusion.

TABLE 10

Experimental Parameters

| Heparin Concentration | 0.75 EU/mL |
| --- | --- |
| Internal diameter of tubing in which device was deployed | 0.25 in. |
| Blood flow rate | 200 mL/min |
| Experiment time | 60-120 min |
| Number of replications (N)** | 6 |

**Blood from a different animal was used in different replications

TABLE 11

Raw Radiation Data for 6 French Polyurethane Control and Hydrogel Formulations

| Raw Radiation counts per minute (CPM) | Raw Radiation counts per minute (CPM) Polyurethane Control | PVA Formulation | PVA w/RO (PVA-barium) | Average |
| --- | --- | --- | --- | --- |
| Expt #1 | 6305 | 8928 | 11509 | 8914 |
| Expt #2 | 9219 | 1803 | 4624 | 5215 |
| Expt #3 | 1194 | 765 | 4101 | 2020 |
| Expt #4 | 8226 | 3095 | 10692 | 7338 |
| Expt #5 | 677 | 2536 | 24837 | 9350 |

TABLE 12

Relative Thrombus Accumulation Based on Percent Difference from Average per Animal

| | % Difference From Average | | |
| --- | --- | --- | --- |
| | Polyurethane Control | PVA Formulation | PVA w/RO (PVA-barium) |
| Expt #1 | −29.27 | 0.16 | 29.11 |
| Expt #2 | 76.77 | −65.43 | 17.71 |
| Expt #3 | −40.89 | −62.13 | 163.87 |
| Expt #4 | 12.11 | −57.82 | 113.99 |
| Expt #5 | −92.76 | −72.88 | 273.46 |
| Mean | −15 | −52 | 120 |
| Std. Error | 44.8 | 20.8 | 74.4 |

The results show a reduction in thrombi for PVA formulation compared to a commercially available PICC. The PVA-RO (barium as RO agent) formulation was not superior to the control. Possible reasons include the lack of barium micronization and evidence of larger barium particles on the surface of die extrusion.

FURTHER DISCLOSURE

1. A process for making a porous solid material comprising heating a mixture that comprises at least one water soluble polymer and a solvent to a temperature above the melting point of the at least one polymer in the polymer-solvent mixture and cooling the mixture in a solvent-removing environment to crosslink the polymer to make a crosslinked matrix, and continuing to remove the solvent until the crosslinked matrix is a microporous solid material or until it is a nanoporous solid material.
2. A process for making a porous solid material comprising heating a mixture that comprises at least one water soluble polymer and a solvent to a temperature above the melting point of the at last one polymer in the mixture, forming the mixture, e.g., by molding or extruding the mixture through a die, and passing the formed mixture into a solvent-removing environment. The process may further comprise one or more of: e.g., cooling the mixture in a solvent-removing environment, and continuing to remove the solvent until the crosslinked matrix is a nanoporous solid material or until it is a microporous solid material.
3. A process for making a porous polymeric material and/or hydrophilic porous solid comprising heating a mixture that comprises at least one water soluble polymer and a solvent to a temperature above a melting point of the polymer, forming the mixture, e.g., extruding the mixture through a die, and passing the formed mixture into a solvent-removing environment. In the case of extrusion, with the polymer forming a continuous porous solid as it passes through the die. Embodiments include removing at least 50% w/w of the solvent in less than 60 minutes (or less than 1, 2, 5, or 10 minutes). Embodiments include removing at least 90% w/w of the solvent in less than 60 minutes (or less than 1, 2, 5, or 10 minutes). Resultant materials may be, e.g., a hydrogel, a microporous material or a nanoporous material. The extrusion may be a cold extrusion.

4. The process of any of 1-3 wherein a salt is in the mixture or is added during the process. Salts can be useful for dissolving polymers and/or to aid in crosslinking. The salt may be, e.g., anionic, cationic, divalent, trivalent. Moreover, additives that are salts or otherwise, that are capable of two or more hydrogen-bond acceptor and/or hydrogen bond donator sites may be added to the polymers.

5. The process of any of 1-4 wherein crosslinking takes place while cooling the mixture and/or in the solvent-removing environment.

6. The process of any of 1-5 wherein the porous solid is crosslinked with bonds that are covalent crosslinks or physical crosslinks. These embodiments include being free of covalent bonds in the case where physical crosslinks are involved.

7. The process of any of 1-6 further comprising annealing the porous solid.

8. The process of any of 1-7 further comprising aligning the polymer chains of the continuous porous solid to be substantially parallel to each other.

9. The process of 8 wherein aligning the polymer chains comprises passing the mixture through a die.

10. The process of any of 1-9 wherein the at least one water soluble polymer comprises PVA, PAA, PEG, PVP-I, or PVP.

11. The process of any of 1-10 wherein the at least one water soluble polymer comprises hydroxyl or carboxyl pendant groups.

12. The process of any of 1-11 wherein the mixture has a concentration of the at least one polymer in the mixture from 5% to 50% w/w of the polymer relative to the mixture.

13. The process of any of 1-11 wherein the mixture has a concentration of the at least one polymer in the mixture from 5% to 50% w/w of the polymer relative to the solvent.

14. The process of 12 wherein at least 50% of the solid material that forms the porous solid is PVA, PAA, PEG, or PVP.

15. The process of any of 1-14 wherein the porous solid completes crosslinking while being in a solvent-removing environment.

16. The process of any of 1-14 wherein the porous solid is prepared as a tube.

17. The process of any of 1-15 wherein exposure to a solvent-removing environment removes at least half of the solvent in less than 60 minutes.

18. The process of any of 1-17 comprising an exposure to a solvent-removing environment of at least one hour. For example, an exposure to the dehydrating environment during which time at least about 50% w/w of the total solvent is removed.

19. The process of any of 1-18 wherein the porous solid has a Young's modulus of at least 5 MPa at EWC.

20. The process of any of 1-18 wherein the porous solid has an elongation at break of at least 200%, a Young's modulus of at least 5 MPa and a tensile strength of at least 20 MPa, at EWC.

21. The process of any of 1-20 wherein the polymeric material further comprises a second material in contact with the porous solid, e.g., the second material being a reinforcing material, a fiber, a wire, or plastic fibers.

22. The process of any of 1-21 wherein the mixture comprises at least two polymers.

23A. The process of any of 1-22 wherein the at least one polymer comprises a first hydrophilic polymer and a second hydrophilic polymer. For example, wherein the first and second polymers are independently chosen from PVA, PAA, PEG, PVP-I, and PVP. And/or for example wherein the first and second polymers are present at a ratio of 1 part of the second polymer and from 1-100,000 parts of the first polymer (w/w).

23B. The process of any of 1-22 wherein the at least one polymer comprises a first polymer at a first concentration and a second polymer at a second concentration, with the first concentration being from 10%-60% w/w and the second polymer being from 1%-10% w/w, with the w/w being the weight of the polymer relative to the total weight of all of the polymers and the solvent in the mixture.

24. The process of any of 1-23 (23 refers to 23A and 23B) wherein the mixture further comprises a salt or other additive for crosslinking.

25. The process of any of 1-24 further comprising an additive capable of two or more hydrogen-bond acceptor and/or hydrogen bond donator sites.

26. The process of any of 22-25 wherein at least two polymers are co-extruded, a for example two or more of: polyvinylpyrrolidone, polyvinylpyrrolidone-iodine, polyethylene glycol, and polyacrylic acid.

27. The process of 26 wherein the coextruded polymers are mixed in a die head.

28. The process of any of 22-26 wherein the water soluble polymer is a first polymer that is formed into a first layer, and further comprising a second polymer formed as a second layer.

29. The process of any of 22-28 wherein the first polymer and the second polymer are extruded at the same time as separate layers.

30. The process of any of 28-29 wherein the first polymer layer is formed as a sheet and the second polymer layer is formed in contact with the sheet.

31. The process of any of 1-31 further comprising adding a third polymer.

32. The process of 31 wherein the third polymer is polyvinylpyrrolidone, polyvinylpyrrolidone-iodine, PEG, or polyacrylic acid.

33. The process of any of 21-32 wherein the second material is a reinforcing material, a fiber, a wire, a braided material, braided wire, braided plastic fibers, or at least a portion of a connector.

34. The process of any of 21-32 further comprising the second material or the second polymer being disposed as a layer on, or within, the material.

35. The process of any of 21-34 wherein the second polymer or the second material comprises a polyethylene glycol or a polyol, e.g., wherein the polyol is a polymer having at least three hydroxyl groups, or wherein the polyol is glycerin.

36. The process of any of 1-35 further comprising adding braiding material in contact with the porous solid.

37. The process of any of 1-36 wherein making the mixture comprises adding PVA to a solvent.
38. The process of any of 1-37 wherein the solvent comprises (or consists essentially of) water, an alcohol, ethanol, an organic solvent miscible with water, or a combination thereof.
39. The process of any of 1-38 wherein the heated solvent is at a temperature from 70 to 120° C.
40. The process of any of 1-39 wherein a PVA concentration in the mixture is from 15% to 25% w/w.
41. The process of any of 1-40 wherein the mixture is cooled after formation or at the time of formation and comprises passing the mixture into a cold bath, a chilled mold, a frozen mold, or liquid nitrogen.
42. The process of any of 1-41 wherein the solvent-removal environment is a chamber filled with a gas. For example, dry air, or nitrogen, or a gas at, e.g., less than atmospheric pressure.
43. The process of any of 1-41 wherein the solvent-removal environment is a solution that comprises ethanol or a polyol.
44. The process of any of 1-41 wherein the solvent-removal environment comprises a solution with an osmolarity that exceeds an osmolarity of the mixture.
45. The process of any of 1-44 wherein the solvent-removal environment or solution comprises a salt present in at a concentration of at least 0.1 molar.
46. The process of any of 44-41 wherein the solvent-removal environment or solution comprises a salt present in at a concentration in a range of 0.1 to 8 molar.
47. The process of any of 1-43 wherein the solvent-removal environment or solution further comprises an osmotic agent, with the environment having an osmolar value greater than an osmolar value of the formed mixture.
48. The process of any of 1-47 wherein the solvent-removal process is performed over a period of time from 3 to 48 hours.
49. The process of any of 1-48 wherein the solvent-removal process is performed while the polymer is crosslinking.
50. The process of 49 wherein the crosslinking is completed before the solvent removal process is completed.
51. The process of any of 1-50 further comprising an annealing process that comprises heating a porous solid material to an annealing temperature.
52. The process of 51 wherein the annealing temperature is from 90 to 250° C.
53. The process of any of 51-52 wherein the annealing is performed in an absence of air and/or oxygen and/or water.
54. The process of any of 50-53 wherein the annealing is performed, at least in part, in a liquid bath.
55. The process of 54 wherein the liquid bath comprises mineral oil and/or a polyol and/or glycerin.
56. The process of any of 50-55 wherein the annealing is performed for a period of time from 3 hours to one week.
57. The process of any of 1-56 wherein the mixture is passed through a die.
58. The process of 57 wherein the mixture is formed as a tube having at least one lumen.
59. The process of 57 wherein the tube is formed around a core.
60. The process of 59 wherein the core is air, water, a liquid, a solid, or a gas.
61. The process of any of 57-60 further comprising a second material or a second polymer being extruded as a layer on, or within, the crosslinked matrix.
62. The process of any of 57-61 wherein the mixture is a first mixture, with the process further comprising a second mixture that comprises a further material, with the second mixture also being passed through the extrusion die to form a second tubular layer.
63. The process of 61 wherein the second material is or comprises a reinforcing material, a fiber, a wire, or plastic fibers.
64. The process of any of 57-63 wherein a solid material surrounds the core and becomes entrapped within the tubular hydrogel layer or, when present, the second tubular layer.
65. The process of 64 wherein the solid material comprises a wire, a braid, a metal wire, a plastic wire, a metal braid, a plastic braid, a mesh, a fabric mesh, a metal mesh, a plastic mesh.
66. The process of any of 1-65 wherein the porous solid is formed as a continuous form, a tube, a sheet, a solid cylinder, a tube with a plurality of lumens, or a ring.
67. The process of any of 1-66 wherein the porous material is with an aspect ratio of at least 4:1 (length: diameter). Alternatively, an aspect ratio from 3:1 to 100:1.
68. The process of any of 1-67 wherein the porous material is hydrophilic.
69. A biomaterial, a polymeric material, or a catheter comprising a medically acceptable hydrophilic porous solid.
70. A biomaterial, a polymeric material, or a catheter comprising a porous polymeric solid having one or more of: a tensile strength of at least 20 MPa, a Young's modulus of at least 5 MPa, a solids content of from 10%-50% w/w at EWC, a solids content of at least 10% w/w or at least 33% at EWC, a solids content of 10, 20, 30, 33, 35, 40, 50, 60% w/w at EWC. For example, a polymeric material comprising a hydrophilic porous solid, with the porous solid having a solids content of at least 33% w/w and a Young's modulus of at least 5 MPa, at equilibrium water content (EWC). And, for example, thrilling with an aspect ratio of at least 10:1. For example, a polymeric material of wherein the porous solid comprises at least one polymer, and the at least one polymer comprises a first hydrophilic polymer and a second hydrophilic polymer, with the second hydrophilic polymer being present in an amount from 1 part to 1,000 parts relative to 10,000 parts of the first polymer.
71. The biomaterial of 69 or 70 wherein the porous polymeric solid comprises crosslinked hydrophilic polymers.
72. The biomaterial of 70 or 71 with the porous polymeric solid having a solids content of at least 33% w/w at equilibrium water content (EWC) in a physiological saline at 37° C. Alternatively, the solids content being at least 50% w/w or in a range from 40% to 99% w/w.
73. The biomaterial of any of 70-72 with being a nanoporous material having a tensile strength of at least 20 MPa and/or a Young's modulus of at least 5 MPa with a solids content of the nanoporous material being at least 50% w/w at EWC.
74. The biomaterial of any of 70-73 wherein the pore diameters are 100 nm or less.
75. The biomaterial of any of 70-74 having an internal alignment of the polymeric structure.

76. The biomaterial of any of 70-75 with the porous material swelling no more than 50% w/w at EWC when placed in an excess of physiological saline and allowed to freely expand, with a PVA content of the hydrogel being at least 50% w/w.

77. The biomaterial of any of 70-76 being a nanoporous material or a microporous material that comprises, or consists essentially of, at least one hydrophilic polymer, PVA, PAA, PEG, or PVP or a combination thereof.

78. The biomaterial of any of 70-77 wherein the porous material comprises a matrix of a crosslinked hydrophilic polymer, wherein the water soluble polymer comprise hydroxyl and/or carboxyl pendant groups.

79. The biomaterial of any of 70-78 wherein the porous material comprises crosslinked polymers having a molecular weight, before crosslinking, of at least 50 k g/mol. Alternatively, a molecular weight in g/mol from 50 k to 1000 k.

80. The biomaterial of any of 70-79 wherein at least 50% of the solid material that forms the porous material is PVA, PAA, PEG, or PVP.

81. The biomaterial of any of 70-80 wherein the porous material is crosslinked with covalent crosslinks or is free of covalent crosslinks and/or is free of covalent crosslinking agents.

82. The biomaterial of any of 70-81 wherein the nanoporous material is crosslinked with physical crosslinks.

83. The biomaterial of 82 wherein the physical crosslinks are ionic bonds, hydrogen bonds, electrostatic bonds, Van Der Waals, or hydrophobic packing.

84. The biomaterial of any of 70-83 further comprising a layer of a second material or a second polymer.

85. The biomaterial of any of 70-83 further comprising a second material encapsulated within the porous solid.

86. The biomaterial of 85 wherein the second material s a reinforcing material, a fiber, a wire, a braided material, braided wire, braided plastic fibers, or at least a portion of a connector.

87. The biomaterial of any of 84-86 wherein the coating or the layer or the second polymer of the second material comprises a polyethylene glycol or a polyol, e.g., wherein the polyol is a polymer having at least three hydroxyl groups, or wherein the polyol is glycerin.

88. The biomaterial of any of 84-87 wherein the coating or the layer or the second polymer of the second material comprises PVA, PAA, PEG, or PVP.

89. The biomaterial of any of 70-88 further comprising a radiopaque (RO) agent. The RO agent may be, e.g., a coating, a layer, on, or in the biomaterial.

90. A biomaterial of any of 70-83 that consists essentially of PVA, or a porous material consists essentially of PVA.

91. The biomaterial of any of 70-91 comprising a shape that is a tube.

92. A biomedical catheter comprising the biomaterial of any of 70-92.

93. The catheter of 92 wherein the catheter is a central venous catheter, a peripherally inserted central catheter (PICC), a tunneled catheter, dialysis catheter. central venous, peripheral central, midline, peripheral, tunneled, dialysis access, urinary, neurological, peritoneal, intra-aortic balloon pump, diagnostic, interventional, or a drug delivery catheter.

94. The catheter of any of 92-93 comprising a plurality of lumens.

95. A biomedical catheter comprising a medically acceptable material, e.g., the material of any of 1-94. For example, a hydrophilic nanoporous material, hydrophilic microporous material, or a hydrogel.

What is claimed is:

1. A hydrophilic porous article, comprising:
   a polymeric material formed by physically crosslinking at least one water soluble polymer to form the hydrophilic porous article, wherein the hydrophilic porous article comprises pores that each have a diameter of 1 µm or less,
   wherein the hydrophilic porous article has a solids content of 33% to 90% w/w at equilibrium water content (EWC) and a Young's modulus of 5-100 MPa at EWC, and wherein the hydrophilic porous article is free of covalent crosslinks between the at least one water soluble polymer that forms the hydrophilic porous article.

2. The hydrophilic porous article of claim 1, wherein the pores of the hydrophilic porous article include interconnected pores.

3. The hydrophilic porous article of claim 1 having an aspect ratio of at least 10:1.

4. The hydrophilic porous article of claim 1 having an aspect ratio of at least 50:1.

5. The hydrophilic porous article of claim 1, wherein at least 50% w/w of the at least one water soluble polymer is poly(vinyl alcohol) (PVA).

6. The hydrophilic porous article of claim 1, wherein the at least one water soluble polymer is selected from the group consisting of poly(vinyl alcohol) (PVA), poly(acrylic acid), polyethylene glycol, and poly(vinyl pyrrolidone).

7. The hydrophilic porous article of claim 1, wherein the at least one water soluble polymer comprises a first hydrophilic polymer and a second hydrophilic polymer, wherein the second hydrophilic polymer is present in an amount from 1 part to 1,000 parts relative to 10,000 parts of the first hydrophilic polymer.

8. The hydrophilic porous article of claim 1, further comprising a radiopaque agent.

9. The hydrophilic porous article of claim 1, wherein the Young's modulus is from 10 to 100 MPa at EWC.

10. The hydrophilic porous article of claim 1, consisting essentially of the at least one water soluble polymer and a radiopaque agent.

11. The hydrophilic porous article of claim 1, wherein a swelling of 50% w/w or less is achieved at EWC.

12. A method for making a hydrophilic porous article, comprising:
    with a polymeric mixture comprising at least one water soluble polymer and a solvent, the polymeric mixture having a concentration of at least 10% w/w of the at least one water soluble polymer, performing the steps of:
    heating the polymeric mixture to achieve a temperature above the melting point of the polymeric mixture,
    extruding the polymeric mixture as an article; and
    removing the solvent from the extruded article at a temperature above a freezing point of the solvent until the article is a porous article, with the article being a porous article that comprises the at least one water soluble polymer, and the porous article is made without covalent crosslinking agents that form covalent crosslinks between polymers extruded to make the porous article.

13. The method of claim 12, wherein, the polymeric mixture is never heated above a boiling point of the polymeric mixture, and the polymeric mixture is extruded at temperatures below a melting point of the polymeric mixture.

14. The method of claim 12, wherein the at least one water soluble polymer comprises a polymer selected from the group consisting of poly(vinyl alcohol) (PVA), poly(acrylic acid), polyethylene glycol, and poly(vinyl pyrrolidone).

15. The method of claim 12, wherein the at least one water soluble polymer comprises a first polymer at a first concentration and a second polymer at a second concentration, with the first concentration being from 10%-60% w/w and the second polymer being from 1%-10% w/w, with the w/w being the weight of the polymer relative to the total weight of all of the polymers and the solvent in the mixture.

16. The method of claim 12, wherein the mixture further comprises a radiopaque agent.

17. The method of claim 12, wherein the porous article is extruded to have an aspect ratio of at least 10:1.

18. The method of claim 12, comprising combining the at least one water soluble polymer and the solvent while heating the polymeric mixture.

19. The method of claim 12, wherein the solvent is selected from the group consisting of water, an alcohol, ethanol, an organic solvent miscible with water, and combinations thereof.

20. The method of claim 12, wherein the article is extruded into a bath, oven, or a chamber filled with gas.

21. The method of claim 12, wherein the solvent is removed from the extruded article without freezing the solvent.

* * * * *